(12) United States Patent
Philp et al.

(10) Patent No.: US 7,563,766 B2
(45) Date of Patent: Jul. 21, 2009

(54) METHODS AND COMPOSITIONS FOR THE PROMOTION OF A HAIR GROWTH UTILIZING ACTIN BINDING PEPTIDES

(75) Inventors: Deborah Philp, Rockville, MD (US); Hynda K. Kleinman, Kensington, MD (US); Michael Elkin, Jerusalem (IL)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 483 days.

(21) Appl. No.: 10/502,115

(22) PCT Filed: Jan. 22, 2003

(86) PCT No.: PCT/US03/01973

§ 371 (c)(1),
(2), (4) Date: Jul. 21, 2004

(87) PCT Pub. No.: WO03/063775

PCT Pub. Date: Aug. 7, 2003

(65) Prior Publication Data

US 2005/0239697 A1     Oct. 27, 2005

Related U.S. Application Data

(60) Provisional application No. 60/351,386, filed on Jan. 25, 2002.

(51) Int. Cl.
*A61K 38/10* (2006.01)
(52) U.S. Cl. .............................. 514/12; 514/13; 514/14
(58) Field of Classification Search ........................ None
See application file for complete search history.

(56) References Cited

U.S. PATENT DOCUMENTS

| | | | | |
|---|---|---|---|---|
| 4,297,276 A | * | 10/1981 | Goldstein et al. | 530/324 |
| 6,030,948 A | | 2/2000 | Mann | |
| 6,855,806 B1 | * | 2/2005 | Prayaga et al. | 530/350 |
| 6,992,170 B2 | * | 1/2006 | Prayaga et al. | 530/350 |
| 2004/0220111 A1 | * | 11/2004 | Kleinman et al. | 514/17 |

FOREIGN PATENT DOCUMENTS

| | | |
|---|---|---|
| EP | 0 103 858 A2 | 3/1984 |
| EP | 0 793 966 A1 | 9/1997 |
| WO | WO 96/11016 A1 | 4/1996 |
| WO | WO 00/06190 * | 2/2000 |
| WO | WO 00/06190 * | 6/2000 |

OTHER PUBLICATIONS

Grant et al., "Matrigel induces thymosin β4 gene in differentiating endothelial cells," *J. Cell Science* 108:3685-3694 (1995).

Huff et al., "β-Thymosins, small acidic peptides with multiple functions," *Int. J. Biochem. Cell Biol*. 33:205-220 (2001).

Kobayashi et al., "Thymosin- β4 regulates motility and metastasis of malignant mouse fibrosarcoma cells," *Am. J. Pathol.* 160:869-882 (2002).

Lee et al., "Hepatocyte growth factor (HGF) activator expressed in hair follicles is involved in in vitro HGF-dependent hair follicle elongation," *J. Dermatol. Sci.* 25:156-163 (2001).

Lindner et al., "Involvement of hepatocyte growth factor/scatter factor and Met receptor signaling in hair follicle morphogenesis and cycling," *FASEB J.* 14:319-332 (2000).

Low et al, "Complete amino acid sequence of bovine thymosin β4: a thymic hormone that induces terminal deoxynucleotidyl transferase activity in thymocyte populations," *Proc. Natl. Acad. Sci.* 78:1162-1166 (1981).

Low and Goldstein, "Chemical characterization of thymosin β4," *J. Biol. Chem.*, 257:1000-1006 (1982).

Malinda et al., "Thymosin $β_4$ stimulates directional migration of human umbilical vein endothelial cells," *FASEB J.* 11:474-481 (1997).

Malinda et al., "Thymosin β4 accelerates wound healing," *J. Invest. Dermatol.* 113:364-368 (1999).

Oh et al., "Hepatocyte growth factor upregulates thymosin β4 in human umbilical vein endothelial cells," *Biochem. Biophys. Res. Commun.* 296:401-405 (2002).

Oshima et al., "Morphogenesis and renewal of hair follicles from adult multipotent stem cells," *Cell* 104:233-245 (2001).

Sato et al., "Induction of the hair growth phase in postnatal mice by localized transient expression of Sonic hedgehog," *J. Clin. Invest.* 104:855-864 (1999).

Shapiro and Price, "Hair regrowth. Therapeutic agents," *Dermatol. Clin.* 16:341-356 (1998).

Taylor et al., "Involvement of follicular stem cells in forming not only the follicle but also the epidermis," *Cell* 102:451-461 (2000).

Yano et al., "Control of hair growth and follicle size by VEGF-mediated angiogenesis," *J. Clin. Invest.* 107:409-417 (2001).

* cited by examiner

*Primary Examiner*—Christopher R. Tate
*Assistant Examiner*—Roy Teller
(74) *Attorney, Agent, or Firm*—Klarquist Sparkman, LLP

(57) ABSTRACT

Disclosed herein are methods and compositions suitable for the promotion of hair growth on humans and other animals. Disclosed embodiments include compositions comprising actin-binding peptides. In some embodiments, the actin-binding peptides comprise fragments of thymosin β4. In other embodiments, the disclosure provides compositions comprising fragments of thymosin β4 and/or other actin-binding peptides that are suitable for the treatment of alopecia and other conditions associated with hair loss. In still further embodiments, the disclosure provides compositions comprising the sequence of approximately six or seven amino acids of the thymosin β4 sequence that bind actin.

9 Claims, 11 Drawing Sheets

Telogen    Early anagen    Peak anagen

SEQUENCE LISTING

```
<160> NUMBER OF SEQ ID NOS: 1

<210> SEQ ID NO 1
<211> LENGTH: 43
<212> TYPE: PRT
<213> ORGANISM: Bos taurus

<400> SEQUENCE: 1

Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ala Gly Glu Ser
        35                  40
```

METHODS AND COMPOSITIONS FOR THE PROMOTION OF A HAIR GROWTH UTILIZING ACTIN BINDING PEPTIDES

CROSS REFERENCE TO RELATED APPLICATION

This is the U.S. National Stage of International Application No. PCT/US03/01973, filed Jan. 22. 2003, which claims the benefit of U.S. Provisional Patent Application No. 60/351,386, filed Jan. 25, 2002, which is hereby incorporated by reference in its entirety.

FIELD

This disclosure provides methods and compositions suitable for the promotion of hair growth on humans and other animals. More particularly, this disclosure relates to methods and compositions for treating a subject suffering from hair loss. In one example, the disclosure relates to the exogenous delivery of the actin-binding moiety of thymosin $\beta_4$ to promote hair growth. In other examples, the disclosure relates to the promotion of hair growth using synthetic or proteolytic peptide fragments containing the actin-binding motif of thymosin $\beta_4$. In still other examples, hair growth is enhanced in a subject by treatment with one or more peptides comprising the seven amino acid residues 17-23 of thymosin $\beta_4$ (referred to herein as "T-3") or the six amino acid residues 17-22 of thymosin $\beta_4$.

BACKGROUND

Hair loss is of concern to a large number of men and women. In many individuals, hair loss (i.e., alopecia) causes embarrassment, and/or psychological problems such as depression. Although alopecia is more common in men (e.g., male pattern baldness or androgenic alopecia) than women (e.g., female pattern baldness), it is a significant concern to both men and women. Indeed, millions of dollars and countless hours of research have been dedicated to solving this problem.

The mature hair follicle is a complex mini-organ that has a tightly regulated growth cycle. During postnatal development, the follicle undergoes successive phases of active hair shaft production (anagen), apoptosis-driven regression (catagen), and a quiescent phase (telogen). Paus et al., "The biology of hair follicles," *NEJM* 341:491-497 (1999). During the anagen phase, active hair growth involves cell proliferation in the proximal follicular epithelium, followed by invasion of the elongating follicle into the subcutaneous tissue, differentiation of the epithelium at the base of the follicle, and formation of hair matrix cells, which proliferate and generate a new hair shaft. When the proliferation capacity of the matrix cells is exhausted, a regression phase (catagen) of the hair growth cycle ensues, through which the lower part of the follicle undergoes programmed cell death and involution. Costsarelis et al., "The hair follicle: dying for attention," *Am. J. Pathol.* 151:1505-1509 (1997). At this point, the follicle enters telogen, the resting period. The cycle is then repeated.

Scalp hair follicles cycle independently of each other. On average, of 100,000 scalp hairs, approximately 90% are in the anagenic (i.e., growth) phase, while the remaining 10% are in the telogenic (i.e., resting) phase, at any given point in time. Whiting, "Disorders of Hair," in Dale and Federman (ed.), *Scientific American Medicine* (from *Web MD Scientific American Medicine*), New York (1999), pages 2:XIII:1-7. The anagen phase lasts an average of about three years, with a range of one to seven years, while the telogen phase lasts an average of about three months, after which the resting hairs are shed and new hairs grow in. The average rate of scalp hair growth is approximately 0.35 mm/day (i.e., approximately 1 inch every 2-3 months). In the anagenic phase, the cells surrounding the dermal papilla actively divide approximately every 12 hours, in order to produce cells which line up, grow longer, and begin to keratinize. During a transition stage (i.e., the catagenic or regression phase) that occurs between the anagen and telogen phases, mitosis no longer occurs and the bulb detaches itself from the papilla and rises towards the surface. In the telogenic phase, the hair is fully keratinized and is ready to be expelled. After three to four months, another mitotic cycle begins in the germination zone of the hair and another hair follicle is formed.

An average loss of 100 scalp hairs/day is considered to be normal, with a higher number being shed on days when the hair is washed. In diagnosing hair disorders, it is important to determine whether the shedding is abnormal and whether shed hairs break off or come out by the roots. Hair normally comes out by the roots. However, trauma or excessive fragility of the hair may cause it to break. In examination of patients, hair pull tests may indicate abnormal shedding. In this test, groups of 10-20 hairs are grasped between the index finger and thumb and pulled steadily. Extraction of more than 20% of the grasped hairs potentially indicates abnormal shedding, usually involving telogen hairs. Telogen hairs ("club hairs") are easily recognized, due to their whitish club-shaped bulbs and lack of root sheaths. Normally, anagen hairs are difficult to detach and have blackish, indented roots with intact root sheaths (Whiting, *Web MD Scientific American Medicine*, pages 2:XIII:1-7 (1999)).

There are various forms of alopecia observed in humans. The most common is androgenetic alopecia, although diffuse alopecia, telogen effluvium, anagen effluvium (i.e., anagen arrest), alopecia areata, traumatic alopecia, trichotillomania, cicatricial alopecia, and other types of hair loss are also observed. In addition, hair loss associated with cancer treatment is quite common and of great concern to a large number of patients. Indeed, treatment with various drugs (e.g., alpha blockers, angiotensin converting enzyme inhibitors, anticoagulants, anticonvulsants, antithyroids, beta blockers, calcium channel blockers, cholesterol reducers, $H_2$ receptor blockers, non-steroidal anti-inflammatories, retinoids, retinol, tricyclic antidepressants, etc.) can result in hair loss for a significant number of patients.

Depending upon the severity, treatment and management of alopecia ranges from continuing observation to medical and surgical treatment, to use of a hairpiece or wig. Topical 2% minoxidil has been approved by the U.S. Food and Drug Administration for use in both men and women. It produces visible hair growth in approximately ⅓ of male and female androgenetic patients, fine-hair growth in approximately ⅓ of patients, and no hair growth in approximately ⅓ of patients. However, it appears to be a relatively effective preventative treatment, as it retards hair loss in approximately 80% of patients. Whiting, *Web MD Scientific American Medicine*, pages 2:XIII: 1-7 (1999). Topical 5% minoxidil produces visible hair growth in 45% of male androgenetic alopecia patients in a shorter time than the 2% solution. Side effects of minoxidil administration include scalp irritation and increased facial hair. In addition, the drug should be used for at least one year to assess whether or not it is effective. If it is effective, use of the medication must be continued indefinitely.

Other compounds that have found use include orally administered finasteride (1 mg/day). At a dosage of 1 mg/day given for 2 years to male patients between 18 and 41 years of age, visible hair growth was observed in 66% of cases and further hair loss was prevented in 83%. Whiting, *Web MD Scientific American Medicine*, pages 2:XIII: 1-7 (1999). However, administration to post-menopausal women was found to be ineffective at a 1 mg/day dosage given over a 1 year period. Side effects of finasteride include lack of libido, lack of potency, and mild reduction in semen. Because of potential severe teratogenic problems for male fetuses, the drug is contraindicated for use by pre-menopausal women.

Additional drugs for treating androgenetic alopecia in women include oral contraceptives (e.g., ethinyl estradiol-ethynodiol diacetate, desogesterl-ethynyl estradiol, and ethinyl estradiol-norgesterimate), which can reduce hair loss and sometimes lead to slight hair growth. Whiting, *Web MD Scientific American Medicine*, pages 2:XIII: 1-7 (1999). Oral spironlactone and dexamethasone have also found use in treatment of female patients.

For other types of alopecia, various approaches include anthralin, psoralen and ultraviolet A, steroids, topical immunotherapy, immunosuppressives, long-term antimicrobial treatment, etc. However, some of these treatment regimes present risks and associated side effects, some of which may be severe.

In cases that do not respond to these compositions, hair transplantation with minigrafts or micrografts may be an option for patients with good reserves of hair on the back and sides of the scalp. In other cases, a hairpiece is the primary option. Indeed, despite the large commitment of resources in the quest for successful treatment and prevention of hair loss, all previously known treatments suffer from serious disadvantages. Thus, there remains a need for compositions and methods to promote hair growth.

The ability of hair follicles to constantly renew is ensured by the presence of multipotent stem cells which, upon division, generate two types of daughter cells. Some of the daughter cells retain the same multipotent phenotype, while others become rapidly-dividing transit-amplifying (TA) cells, which provide differentiated progeny for the regeneration of the lower follicle at the onset of each new cycle and formation of the hair shaft. Janes et al., "Epidermal stem cells," *J. Pathol.* 197:479-494 (2002). Recently, the bulge region of the follicle, located close to the insertion of the arrector pili muscle, has been identified as a stem cells "niche." See Lyle et al., "Human follicle bulge cells are biochemically distinct and possess an epithelial stem cell phenotype," *J. Invest. Dermatol Synip. Proc.* 4:296-301 (1999); Taylor et al., "Involvement of follicular stem cells in forming not only the follicle but also the epidermis," *Cell* 102:453-461 (2000); Oshima et al., "Morphogenesis and renewal of hair follicles from adult multipotent stem cells," *Cell* 104:233-245 (2001). At the onset of anagen, bulge-localized, multipotent stem cells or their TA daughter cells migrate to the base of the follicle to become matrix cells and to produce a new hair shaft. Interestingly, cells emanating from the bulge region migrate downward to repopulate the hair matrix and also migrate upwards to replenish the skin epithelium, and may therefore contribute to wound healing processes.

Thymosin $\beta_4$, an ubiquitous 4.9 kDa polypeptide originally isolated from bovine thymus, is a potent mediator of some types of cell migration and differentiation. See Low et al, "Complete amino acid sequence of bovine thymosin: a thymic hormone that induces terminal deoxynucleotidyl transferase activity in thymocyte populations," *Proc. Natl. Acad. Sci.* 78:1162-1166 (1981); Grant et al., "A novel role for thymosin beta4: a Matrigel-induced gene involved in endothelial cell differentiation and angiogenesis," *J. Cell Science* 108:3685-3694 (1995); Malinda et al., "Thymosin $\beta_4$ stimulates directional migration of human umbilical vein endothelial cells," *FASEB J.* 11:474-481 (1997); Malinda et al., "Thymosin $\beta 4$ accelerates wound healing," *J. Invest. Dermatol.* 113:364-368 (1999); Sosne et al., "Thymosin beta 4 promotes corneal wound healing and decreases inflammation in vivo following alkali injury," *Ex. Eye Res.* 74:293-299 (2002). Thymosin $\beta_4$ was identified with a gene that is upregulated four- to six-fold during early endothelial cell tube formation and was later shown to promote angiogenesis. It is present in wound fluid, and when added topically or given systemically it promotes angiogenesis and wound healing. See Frohm et al., "Biochemical and antibacterial analysis of human wound and blister fluid," *Eur. J. Biochem.* 237:86-92 (1996); Malinda et al., *J. Invest. Dermatol.* 113:364-368 (1999). It is also a potent anti-inflammatory. Sosne et al., *Ex. Eye Res.* 74:293-299 (2002); Frohm et al., *Eur. J. Biochem.* 237:86-92 (1996); Young et al., "Thymosin beta 4 sulfoxide is an anti-inflammatory agent generated by monocytes in the presence of glucocoticoids," *Nat. Med.* 5:1424-1427 (1999). Moreover, thymosin $\beta_4$ is present at increased levels in metastatic tumors and when transfected into low metastatic cells, it increases malignancy. Clark et al., "Genomic analysis of metastasis reveals an essential role for RhoC," *Nature* 406:532-535 (2000); Kobayashi et al., "Thymosin-beta4 regulates motility and metastasis of malignant mouse fibrosarcoma cells," *Am J. Pathol.* 160:869-882 (2002). A related family member, thymosin $\beta_{15}$, is also important in metastasis of certain tumor types. Bao et al., "Thymosin beta 15: a novel regulator of tumor cell motility upregulated in metastatic prostate cancer," *Nat. Med.* 2:1322-1328 (1996); Bao et al., "Thymosin beta 15 expression in tumor cell lines with varying metastatic potential," *Clin. Exp. Metastasis* 16:227-233 (1998). The metastatic activity of thymosin $\beta_4$ may be related to its angiogneic and migration-promoting activities as well as to its potential to inhibit immune surveillance. Recently, thymosin $\beta_4$ was found to be a potent antimicrobial. Tung et al., "Antimicrobial peptides from human platelets," *Infect. Immnwz.* 70:6524-6533 (2002).

Thymosin $\beta_4$ typically acts by accelerating the migration of endothelial cells and keratinocytes, and increasing the production of extracellular matrix-degrading enzymes.

SUMMARY OF THE DISCLOSURE

The present disclosure demonstrates the role of thymosin $\beta_4$ in hair growth in different in vitro and in vivo experimental models. Thymosin $\beta_4$ promotes hair growth in both aged and nude mouse models as well as in normal rats. Without being bound to any particular theory, a specific subset of follicular keratinocytes in the mouse skin, which originate at the bulge region, express thymosin $\beta_4$ in a highly coordinated manner during the different stages of the hair growth cycle. Temporal and spatial distribution of these keratinocytes parallels the pattern previously proposed by Taylor et al., *Cell* 102:453-461 (2000), for the stem cells and their daughter TA cells at the different stages of the hair cycle. When isolated from the bulge compartment of the rat vibrissa follicle, the clonogenic keratinocytes were further characterized as an immediate progeny of the stem cells and found to express high levels of thymosin $\beta_4$ when cultured in vitro. Thymosin $\beta_4$ was found to promote hair clonogenic keratinocyte cell migration, as well as secretion of the extracellular matrix-degrading enzyme MMP-2. Taken together, the results show that in addition to its known angiogenic and wound healing properties, thymosin $\beta_4$ is a naturally occurring modulator of hair growth.

Disclosed herein are methods for promoting hair growth in humans and other animals by administering to the subject a therapeutically effective amount of a peptide containing the actin-binding moiety of thymosin $\beta_4$ ("T$\beta$4"), that portion of the sequence of the thymosin $\beta_4$ sequence which binds actin (such as T-3 or residues 17-22) or any other actin-binding polypeptide. In certain tests, T$\beta$4 was administered topically in a hydrogel mixture. In one non-limiting example, T-3 is administered in a therapeutically effective amount.

The disclosure further provides a minimal fragment of the thymosin $\beta_4$ sequence that is associated with hair growth, for example the "T-3" fragment (residues 17-23) or the shorter actin binding sequence (residues 17-22). These fragments, or petides comprising these sequences, are used to promote hair growth on humans and other animals. In some embodiments, a peptide comprising one or more of these sequences is applied topically to the area to be treated. In other embodiments, the peptide is applied in conjunction with additional compositions, including but not limited to antimicrobials, antiparasitics, skin and/or hair conditioners, soaps, emollients, and other suitable compositions. In additional embodiments, T-3 is applied in conjunction with a carrier and/or gel. In still other embodiments, T-3 is applied in conjunction with a hydrogel.

In still further embodiments, the present disclosure provides actin-binding domains that find use in promoting hair growth. It is also contemplated that variants or homologues of these sequences (e.g., with conservative and/or non-conservative amino acid changes) will find use in promoting hair growth. Alternatively, the peptides include full-length T$\beta$4 sequences, with one or more conservative substitutions outside of the actin binding sequence (residues 17-22). Polymers of actin-binding polypeptide moieties (for example dimers and trimers of T$\beta$4, T-3 or a peptide containing the sequence of amino acids 17-22 of T$\beta$4) can also show enhanced hair growth activity, as can any of several fusion molecules bonded to an actin-binding moiety. Thus, an actin-binding moiety useful in the present disclosure may be expressed in many ways, including as part of a larger peptide, as part of a fusion molecule, or in a polymer or combinations thereof.

Moreover, in another embodiment, the exogenous addition of thymosin $\beta_4$ to isolated clonogenic hair follicle stem cells leads to increased migration and enhanced matrix metalloproteinase (MMP) activity (and, specifically, increased MMP-2 levels). In this and related embodiments, hair follicle stem cells can be activated, promoting differentiation but not proliferation. In certain embodiments, many activities important for hair growth are promoted in stem cells, including migration, protease production and differentiation.

Sonic hedgehog has been shown to promote hair follicles to enter the anagen phase. Sato et al., "Induction of the hair growth phase in postnatal mice by localized transient expression of Sonic hedgehog," *J. Clin. Invest.* 104:855-864 (1999). Shh signaling intersects and influences the Wnt signaling pathway which is involved in hair growth. T$\beta$4 is present in the nuclei of clonogenic keratinocytes and likely regulates signaling. While not being bound by theory, an actin-binding moiety of thymosin $\beta_4$ may, in certain embodiments, activate sonic hedgehog expression, which in turn promotes hair follicles to enter the anagen phase.

Vascular endothelial growth factor ("VEGF"), like actin-binding domains of thymosin $\beta_4$, is angiogenic. Hair follicles induced by either VEGF or thymosin $\beta_4$ are larger in size. See Yano et al., "Control of hair growth and follicle size by VEGF-mediated angiogenesis," *J. Clin. Invest.* 107:409-417 (2001). Thus, in certain embodiments, an actin-binding domain of the thymosin $\beta_4$ sequence, T-3 or other actin-binding peptides enhances hair growth and/or follicle size by promoting angiogensis. The peptides disclosed herein may also be used in combination (simultaneously or sequentially) with other hair growth promoting compositions (either topically or orally administered) such as minoxidil or finisteride. While not being bound to any theory, an actin-binding moiety of thymosin $\beta_4$ may, in certain embodiments, activate VEGF expression, which in turn promotes hair follicles to enter the anagen phase.

BRIEF DESCRIPTION OF THE FIGURES

FIGS. 7A-7C are control vehicle-treated skin. FIGS. 7D, 7E show thymosin $\beta_4$-treated skin. FIGS. 7A, 7D both show rat skin after 7 days of treatment. FIGS. 7B, 7E show aged mouse skin after 7 days of treatment. FIGS. 7C, 7F show nude mouse skin after 35 days of treatment.

FIG. 9A is a photomicrograph showing the location of the bulge region with an insert/blow-up showing immunostaining with anti-keratin 15 antibody. (Keratin 15 is a molecular marker for hair follicle stem cells. Keratins 5 and 14 are also known to be expressed in stem cells.) FIG. 9B shows the culture of stem cells after 6 days. Note that two clonogenic populations are observed. FIG. 9C is an immunostain of the stem cells with the antibody to thymosin $\beta_4$.

SEQUENCE LISTING

Figure 1:
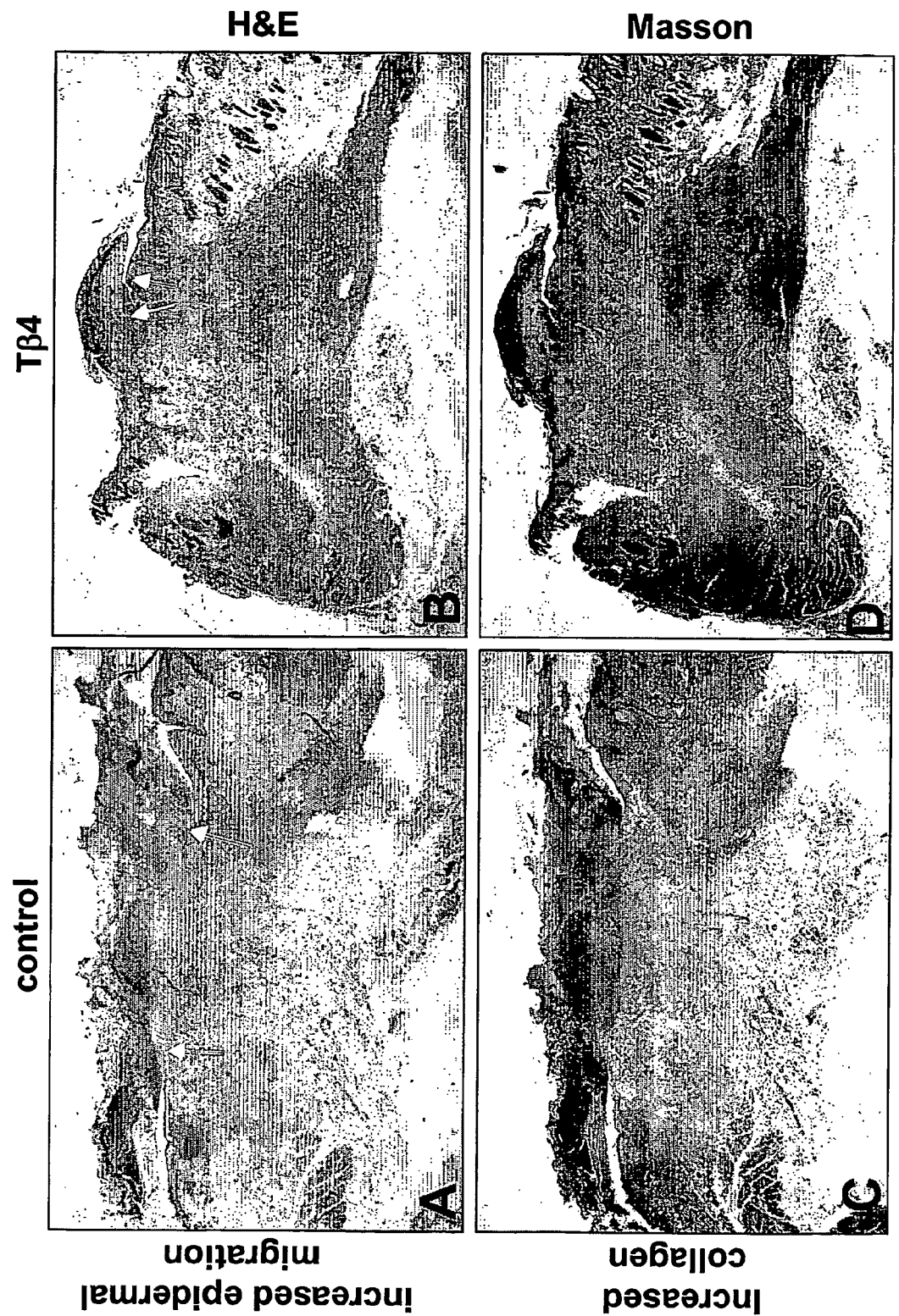
FIGS. 1A-1D are digital images of photomicrographs of histology sections of rat skin, showing increased wound closure after 7 days and additional hair follicles at wound margin after treatment of skin with thymosin $\beta_4$.

The amino acid sequence listed in the accompanying sequence listing are shown using standard three letter code for amino acids, as defined in 37 C.F.R. 1.822. In the accompanying sequence listing T$\beta$4 is given as SEQ ID NO: 1: Ser Asp Lys Pro Asp Met Ala Glu Ile Glu Lys Phe Asp Lys Ser Lys Leu Lys Lys Thr Glu Thr Gin Glu Lys Asn Pro Leu Pro Ser Lys Glu Thr Ile Glu Gin Glu Lys Gin Ala Gly Glu Ser.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a protein" includes a plurality of such proteins and reference to "the antibody" includes reference to one or more antibodies and equivalents thereof known to those skilled in the art, and so forth.

Unless explained otherwise, all technical and scientific terms used herein have the same meaning as commonly understood to one of ordinary skill in the art to which this disclosure belongs.

Abbreviations: ° C. (degrees Centigrade); $H_2O$ (water); aa or AA (amino acid); bp (base pair); kb (kilobase pair); kD or kDa (kilodaltons); gm (grams); μg (micrograms); mg (milligrams); ng (nanograms); μl or μL (microliters); ml or mL (milliliters); mm (millimeters); nm (nanometers); μm (micrometer); M (molar); mM (millimolar); μM (micromolar); U (units); MW (molecular weight); sec (seconds); min(s) (minute/minutes); hr(s) (hour/hours); BSA (bovine serum albumin); PAGE (polyacrylamide gel electrophoresis); PBS (phosphate buffered saline [150 mM NaCl, 10 mM sodium phosphate buffer, pH 7.2]); PCR (polymerase chain reaction); RT (room temperature); SDS (sodium dodecyl sulfate); w/v (weight to volume); v/v (volume to volume); H&E (Hematoxylin and Eosin stain); HEPES (N-2-Hydroxyethylpiperazine-N'-2-ethanesulfonic acid); HUVEC (human umbilical vein endothelial cells); Sigma (Sigma Chemical Co., St. Louis, Mo.); American Histolabs (American Histolabs, Gaithersburg, Md.); and Hawkeye-Jensen, Inc. (Hawkeye-Jensen, Inc., Reading, Pa.).

Actin-Binding Peptide: A peptide that binds actin and promotes hair growth, including, but not limited to, those peptides containing the T-3 sequence of amino acids, the sequence of amino acid residues 17-22 contained in T$\beta$4, the sequence of amino acids Leu Lys Lys Thr Asn Thr, the sequence of amino acids Leu Lys Lys Thr Asn Thr Glu, and peptides comprising any of the foregoing sequences with up to 2 conservative amino acid substitutions. One skilled in the art can readily identify additional related actin-binding peptides, which can find use in the present disclosure, by the techniques described in Example 10. For example, actin-binding peptides can be identified as those peptides whose vessel sprouting activity is inhibited by the addition of exogenous actin. In some embodiments, useful actin-binding peptides form a complex with G-actin with dissociation constants greater than about 0.3 μM, or more often, greater than 0.5 μM or in the range 0.5-2.5 μM.

Alopecia: Hair loss (i.e., baldness or hair thinning) from areas where hair is normally present. It is intended that the term encompass hair loss that results from any cause. In preferred embodiments, the term refers to the loss of scalp hair, although it is not intended to be so limited. Indeed, it is intended that the term encompass full or partial hair loss, shedding or any decrease in the number of follicles or follicles in the anagen phase at any body site where hair is normally present.

Chemical synthesis: An artificial means by which one can make a protein or peptide. A synthetic protein or peptide is one made by such artificial means.

Comprises: A term that means "including." For example, "comprising A or B" means including A, B, or both A and B, unless clearly indicated otherwise.

Enhance: To improve the quality, amount, or strength of something. In one embodiment, a treatment enhances or increases hair growth in a subject (e.g., a person suffering from alopecia or other conditions associated with hair loss) if the subject's hair loss is retarded, stopped or reversed (i.e., the number of follicles increases or the number of follicles in the anagen phase increases). Enhanced hair growth also includes decreased shedding, either at the roots or by breaking/fragility, measured, for example, by hair pull tests. Any enhancement can be measured using any method known in the art or any of the methods disclosed herein, for example, quantitative and qualitative comparison of treated areas or subjects to controls.

Fragment: A "fragment" of T$\beta$4, T-3 or any other peptide comprises any sequence of amino acid residues less than the full length sequence. Thus, a fragment of T$\beta$4 would comprise a sequence of up to 42 residues contained in SEQ ID NO: 1. Likewise, a fragment of T-3 comprises a sequence of up to 6 amino acid residues contained in the sequence defined herein as T-3.

Hair: The specialized keratinized structures derived or protruding from invaginations of the epidermal epithelium that are observed on animals, including mammals. Thus, the term is also intended to encompass hair coats (e.g., fur) of various non-human animals.

Homologous: Describes related proteins. In some preferred embodiments, the term is used in reference to various actin-binding peptides disclosed herein, as well as other proteins/peptides that share similar sequences, structure, function, and/or other characteristics. See the discussion within the definition of "sequence identity/similarity."

Hydrogel: Any hydrogel comprising any of various polymers. In the medical field, many proprietary hydrogel formulations are known. In certain embodiments, hydrogel sheets of cross-linked polymer gels are used. It is contemplated that hydrogels from various sources will find use with the present methods and compositions, including, but not limited to commercially available hydrogels, including those suitable for use with wounds, such as TEGAGEL® (3M), VIGELON® (Bard), CLEARSITE® (Conmed), AQUASORB® (DeRoyal), FLEXDERM® (Bertek [Dow Hickam]), NU-GEL® (Johnson & Johnson), CURAGEL® (Kendall), DERMA-GEL® (Medline Industries), FLEXIGEL® (Smith & Nephew), SMART HYDROGEL™ (MedLogic Global, United Kingdom), and 0.2% polyacrylic acid (Hawkeye-Jensen, Reading Pa.).

Local: "Localized" and "local" refer to the involvement of a limited area. Thus, in contrast to "systemic" treatment, in which the entire body is involved (usually through the vascular and/or lymph systems), "localized treatment" involves the treatment of a specific, limited area. Thus, in some embodiments herein, discrete areas are treated locally and/or topically using the methods and compositions of the present disclosure.

Pharmaceutically Suitable Carrier: Any of the many vehicles known and used in the art for delivering drugs, pharmaceuticals and the like to a subject. Herein, a pharmaceutically suitable carrier may be especially appropriate for delivery in topical applications, including without limitation hydrogels, creams, lotions, shampoos, emollients, 85% ethanol/15% ethylene glycol, salves, sprays, oils, dressings, pastes, drops, ointments, liposomes, and the like.

Polypeptide, or just peptide, refers to a polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The terms "polypeptide" and "peptide" are specifically intended to cover naturally occurring proteins, as well as those that are recombinantly or synthetically produced. Accordingly, Tβ4, T-3, a peptide containing the amino acid sequence of residues 17-22 of Tβ4, or a polymer of any of those sequences may be synthesized recombinantly, including in bacteria or yeast cells.

The term "functional fragments of a polypeptide" refers to all fragments of a polypeptide that retain an activity of the polypeptide, such as a Tβ4. Biologically functional fragments, for example, can vary in size from a polypeptide fragment as small as an epitope capable of binding an antibody molecule to a large polypeptide capable of participating in the characteristic induction or programming of phenotypic changes within a cell, including affecting cell proliferation or differentiation. An "epitope" is a region of a polypeptide capable of binding an immunoglobulin generated in response to contact with an antigen.

The term "soluble" refers to a form of a polypeptide that is not inserted into a cell membrane. The polypeptides disclosed herein can be soluble polypeptides.

The term "substantially purified polypeptide" as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below.

| Original Residue | Conservative Substitutions |
| --- | --- |
| Ala | Ser, Gly |
| Arg | Lys |
| Asn | Gln, His |
| Asp | Glu |
| Cys | Ser |
| Gln | Asn, Glu |
| Glu | Asp |
| His | Asn; Glu |
| Ile | Leu, Val |
| Leu | Ile; Val, Arg |
| Lys | Arg; Gln; Glu |
| Met | Leu; Ile, Val |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, are ideally minimized in order to preserve the functional and immunologic identity of the encoded protein. Thus, in several non-limiting examples, a variant polypeptide includes at most two, at most five, at most ten, at most twenty, or at most forty conservative substitutions. The immunologic identity of the protein may be assessed by determining whether it is recognized by an antibody, a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence.

Promote: To be interpreted in the same way as "enhance" defined herein.

Sample and Specimen: In the present specification and claims, these terms are used in their broadest sense. These terms encompasses all types of samples obtained from humans and other animals, including but not limited to, body fluids such as urine, blood, fecal matter, cerebrospinal fluid, semen, and saliva, as well as solid tissue and hair. However, these examples are not to be construed as limiting the sample types applicable to the present disclosure.

Sequence Identity/Similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482 (1981); Needleman & Wunsch, *J. Mol. Biol.* 48:443 (1970); Pearson & Lipman, *Proc. Natl. Acad. Sci. USA* 85:2444 (1988); Higgins & Sharp, *Gene*, 73:23744 (1988); Higgins & Sharp, *CABIOS* 5:151-3 (1989); Corpet et al., *Nuc. Acids Res.* 16:10881-90 (1988); Huang et al., *Computer Appls. in the Biosciences* 8:155-65 (1992); and Pearson et al., *Meth. Mol. Bio.* 24:307-31 (1994). Altschul et al., *J. Mol. Biol.* 215:403-10 (1990), presents a detailed consideration of sequence alignment methods and homology calculations.

The NCBI Basic Local Alignment Search Tool (BLAST) (Altschul et al., *J. Mol. Biol.* 215:403-10 (1990)) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, for example 75%, 80%, 85%, 90%, 95%, or even 99% sequence identity. When less than the entire sequence is being compared for sequence identity, homologs will typically possess at least 75% sequence identity over short windows of 10-20 amino acids, for example sequence identities of at least 85%, 90%, 95% or 98% depending on their identity to the reference sequence. Methods for determining sequence identity over such short windows are described at the NCBI web site.

Protein homologs are typically characterized by possession of at least 70%, for example at least 75%, 80%, 85%, 90%, 95% or even 98% sequence identity, counted over the full-length alignment with the amino acid sequence using the NCBI Basic Blast 2.0, gapped blastp with databases such as the nr or swissprot database. Queries searched with the blastn program are filtered with DUST (Hancock and Armstrong, *Comput. Appl. Biosci.* 10:67-70 (1994)). Other programs use SEG.

One of skill in the art will appreciate that these sequence identity ranges are provided for guidance only; it is possible that strongly significant homologs could be obtained that fall outside the ranges provided. Provided herein are the peptide homologs described above, as well as nucleic acid molecules that encode such homologs.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous peptides can, for example, possess at least 75%, 80%, 90%, 95%, 98%, or 99% sequence identity determined by this method. When less than the entire sequence is being compared for sequence identity, homologs can, for example, possess at least 75%, 85% 90%, 95%, 98% or 99% sequence identity over short windows of 10-20 amino acids. Methods for determining sequence identity over such short windows can be found at the NCBI web site. One of skill in the art will appreciate that these sequence identity ranges are provided for guidance only, it is possible that significant homologs or other variants can be obtained that fall outside the ranges provided.

Subject: Living multicellular vertebrate organisms, which includes both human and veterinary subjects, for example mammals, rodents, and birds.

Therapeutically Effective Amount: An amount sufficient to achieve a desired biological effect, for example an amount that is effective to enhance hair growth. In particular examples, it is a concentration of T$\beta$4, T-3 or other actin-binding peptide effective to enhance hair growth such as in a subject to whom it is administered or any other living or non-living sample containing hair follicles.

A therapeutically effective amount can be administered in a single dose or in several doses, for example daily, during a course of treatment.

The methods disclosed herein have equal application in medical and veterinary settings. Therefore, a general term such as "subject being treated" should be understood to include all animals (e.g., humans, apes, dogs, cats, horses, and cows) that require an increase in the desired biological effect, such as enhanced hair growth, increased clonogenic stem cell migration, increased stem cell migration or enhanced matrix metalloproteinase (MMP) activity.

Therapeutically Effective Homolog: A homologous sequence that enhances hair growth in a subject at some "therapeutically effective amount."

Thymosin $\beta_4$: A small protein of 43 amino acids (Ser Asp Lys Pro Asp Met Ala Glu Ile Glu Lys Phe Asp Lys Ser Lys Leu Lys Lys Thr Glu Thr Gln Glu Lys Asn Pro Leu Pro Ser Lys Glu Thr Ile Glu Gln Glu Lys Gln Ala Gly Glu Ser; SEQ ID NO: 1). It is intended that the term encompass native, recombinant and synthetic thymosin $\beta_4$. Also referred to herein as T$\beta$4 or T$\beta_4$.

T-3: The seven amino acid sequence Leu Lys Lys Thr Glu Thr Gln corresponding to amino acids 17-23 of the full-length T$\beta$4 sequence (i.e., SEQ ID NO: 1). It is intended that the term encompass native, recombinant and synthetic T-3.

Topically Applied: Application to the surface of the skin, mucosa, viscera, hair, etc. In other words, not ingested or injected.

Topically Active Agent: A substance or composition which causes a pharmacological response or biological effect at the site of application.

Variant: A "variant" generally refers to a homologous peptide.

A "variant" of thymosin $\beta_4$ refers to an amino acid sequence similar to the sequence encoding thymosin $\beta_4$ that is altered by one or more amino acids (i.e., in comparison to the sequence set forth in SEQ ID NO: 1). Thus, the "variant" will have less than 100% sequence identity with T$\beta$4. The variant may have "conservative" changes, wherein a substituted amino acid has similar structural or chemical properties (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art and discussed above in connection with "sequence identity/similarity" above.

Similarly, a "variant" of T-3 is an amino acid sequence similar to the fragment of thymosin $\beta_4$ representing amino acids 17-23 but is altered by one or more amino acids. As with variants of thymosin $\beta_4$, the changes may be conservative or non-conservative.

Any amino acid sequence or fragment described herein has, in the same way, "variants."

DESCRIPTION

The present disclosure relates to methods and compositions suitable for promoting hair growth on humans and other animals. In particular, the present disclsoure provides compositions comprising actin-binding peptides. In some embodiments, the actin-binding peptides comprise fragments of thymosin $\beta_4$. In some preferred embodiments, the present disclosure provides compositions comprising one or more thymosin $\beta_4$ fragments and/or other actin-binding peptides that are suitable for the treatment of alopecia and other conditions associated with hair loss. In some particularly preferred embodiments, the present disclosure provides compositions comprising the sequence of the six or seven amino acids of the thymosin $\beta_4$ sequence which bind actin.

Thymosin $\beta_4$ is a small protein of 43 amino acids (Ser Asp Lys Pro Asp Met Ala Glu Ile Glu Lys Phe Asp Lys Ser Lys Leu Lys Lys Thr Glu Thr Gln Glu Lys Asn Pro Leu Pro Ser Lys Glu Thr Ile Glu Gln Glu Lys Gln Ala Gly Glu Ser; SEQ ID NO: 1) (Low and Goldstein, *J: Biol. Chem.*, 257:1000 (1982)). It is found at concentrations of $1 \times 10^{-5}$ to $5.6 \times 10^{-1}$ M in a variety of tissues and cell types. Thymosin $\beta_4$ is a minor (typically about 1%) component of "thymosin fraction 5" (TF5), a partially purified mixture of polypeptides prepared from thymus glands of various animals (e.g., bovine, porcine, murine, caprine, rat, chicken, and humans). TF5 can be prepared using any suitable means known in the art. TF5 is known to be composed of at least 40-50 distinct polypeptides observable in isoelectric focusing polyacrylamide gels (pH 3.5-9.5), and is essentially free of lipids, carbohydrates and endotoxins. See, e.g., Hooper et al., *Ann. NY Acad. Sci.* 249:125 (1975). TF5 has been shown to be effective in reconstituting immune functions in thymic-deprived or immunodeprived animals, in humans with primary immunodeficiencies, and in imunosuppressed cancer patients.

Thymosin $\beta_4$ can interact with G-actin and is a major actin sequestering protein in cells. Thymosin $\beta_4$ is active for endothelial and keratinocyte cell migration in vitro and angiogenesis in vivo. Thymosin $\beta_4$ has also been found to greatly accelerate full thickness wound repair in the skin of rats in both normal animals and in models of impaired healing (i.e., steroid treated rats, diabetic mice, and aged mice). The wound depth and width were greatly reduced in animals treated with either topical or systemic thymosin $\beta_4$. In addition, collagen deposition was increased, likely due to the increased blood supply to the early wounds. The thymosin $\beta_4$ concentration is highest in platelets which are among the first cells to enter wounds and to release the contents of their granules containing repair factors and molecules responsible for recruiting additional cells to the wound site. However, an understanding of mechanisms is not necessary in order to use the methods and compositions of the present disclosure.

Thymosin $\beta_4$ is also present in wound fluid. It is different from other repair factors, such as growth factors, in that it: (1) promotes endothelial and keratinocyte migration; (2) does not bind to the matrix and is very low molecular weight (allowing it to diffuse relatively long distances through tissues); and (3) does not promote cell growth.

The exogenous addition of thymosin $\beta_4$ or an actin-binding fragment thereof, to isolated clonogenic hair follicle stem cells leads to increased migration and enhanced matrix metalloproteinase (MMP) activity (and, specifically, increased MMP-2 levels). Thus, hair follicle stem cells are activated, promoting differentiation but not proliferation. By the methods disclosed herein, many activities important for hair growth are promoted in stem cells, including migration, protease production and differentiation.

Sonic hedgehog has been shown to promote hair follicles to enter the anagen phase. Sato et al., "Induction of the hair growth phase in postnatal mice by localized transient expression of Sonic hedgehog," *J. Clin. Invest.* 104:855-864 (1999). Shh signaling intersects and influences the Wnt signaling pathway, which is involved in hair growth. Thymosin $\beta_4$ is present in the nuclei of clonogenic keratinocytes and likely regulates signaling. Not being bound by the theory, thymosin $\beta_4$ may, in certain embodiments, activate sonic hedgehog, which, in turn, promotes hair follicles to enter the anagen phase.

Vascular endothelial growth factor ("VEGF"), like thymosin $\beta_4$, is angiogenic. Hair follicles induced by either VEGF or thymosin $\beta_4$ are larger in size. See Yano et al., "Control of hair growth and follicle size by VEGF-mediated angiogenesis," *J. Clin. Invest.* 107:409-417 (2001). Thus, in certain embodiments, fragments of thymosin $\beta_4$, T-3 or other actin-binding peptides enhance hair growth and/or follicle size by angiogensis. Not being bound by the theory, T$\beta$4 may, in certain embodiments, activate VEGF expression, which in turn increases angiogenesis and hair growth.

Recently, another angiogenic molecule expressed in hair follicles, hepatocyte growth factor, has also been found to promote hair growth. Grant et al., "Scatter factor induces blood vessel formation in vivo," *Proc. Natl. Acad. Sci USA* 90:1937-1941 (1993); Lee et al., "Hepatocyte growth factor (HGF) activator expressed in hair follicles is involved in vitro HGF-dependent hair follicle elongation," *J. DermatoL Sci.* 25:156-163 (2001); Lindner et al., "Involvement of hepatocyte growth factor/scatter factor and met receptor signaling in hair follicle morphogenesis and cycling," *FASEB J.* 14:319-332 (2000). Hepatocyte growth factor also upregulates thymosin $\beta_4$ expression. Oh et al., "Hepatocyte growth factor upregulates thymosin beta4 in human umbilical vein endothelial cells," *Biochem. Biophys. Res. Conmnmun.* 296:401-405 (2002). Thus, the use of hepatocyte growth factor to promote hair growth may in fact mimic or duplicate the methods disclosed herein if it is acting by increasing thymosin $\beta_4$ and/or synergizing with it.

Furthermore, steroids have been used to treat certain types of hair loss. Shapiro et al., "Hair regrowth. Therapeutic agents," *Dermatol. Clin.* 16:341-356 (1998). Thymosin $\beta_4$ is an anti-inflammatory molecule that has been identified in steroid-treated monocytes. Young et al., *Nat. Med.* 5:1424-1427 (1999). Therefore, treatment with steroids may also involve the activity of thymosin $\beta_4$ on hair growth.

Together these data support the conclusion and results indicating that the actin-binding domain of thymosin $\beta_4$ is a naturally occurring wound repair factor and angiogen, i.e., promoter and modulator of hair growth.

As described in further detail in the Examples, during the development of the present methods and compositions, wound healing experiments were conducted on female rats. In these experiments, a hydrogel formulation (0.2% polyacrylic acid) containing thymosin $\beta_4$ was applied to wounds. Control animals received gel alone. When the wounds were examined visually at day 7 after wounding, increased hair growth around the wound site was clearly observed. The hair growth visually appeared longer and denser than the surrounding hair in other shaved areas of the animal. After 7 days, the animals were sacrificed and tissue sections of the area where the gel was applied were prepared and stained using methods known in the art (H&E and Masson's trichrome stains). As shown in FIG. 1, there was an increase in the number of hair follicles observed at the edge of the healing wounds treated with thymosin β₄.

Figure 2:
FIGS. 2A-2D are digital images of photomicrographs showing that thymosin $\beta_4$ in hydrogel stimulates new hair growth on rat skin at 7 days post treatment.
Figure 2:
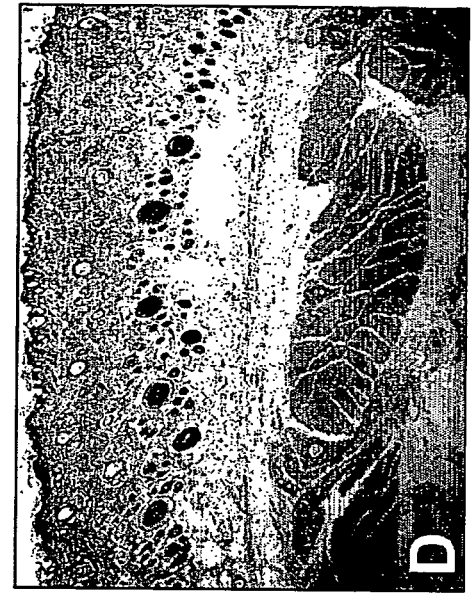
Figure 2:
Figure 2:
Figure 3:
FIGS. 3A-3D are digital images of photomicrographs showing that thymosin $\beta_4$ in hydrogel stimulates new hair growth on rats at 30 days post treatment. Hematoxylin and Eosin ("H&E") stain was used.
Figure 3:
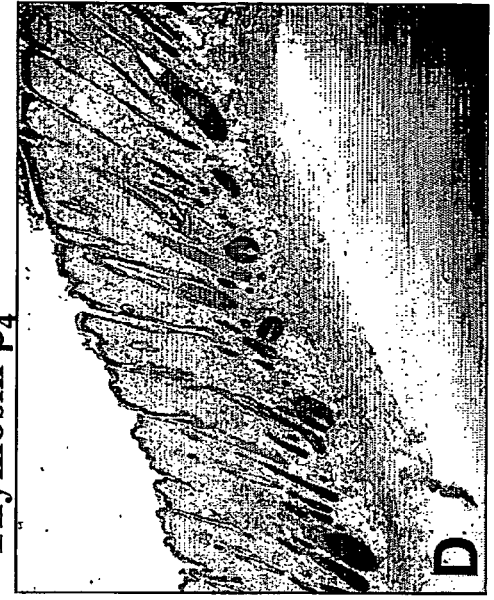
Figure 3:
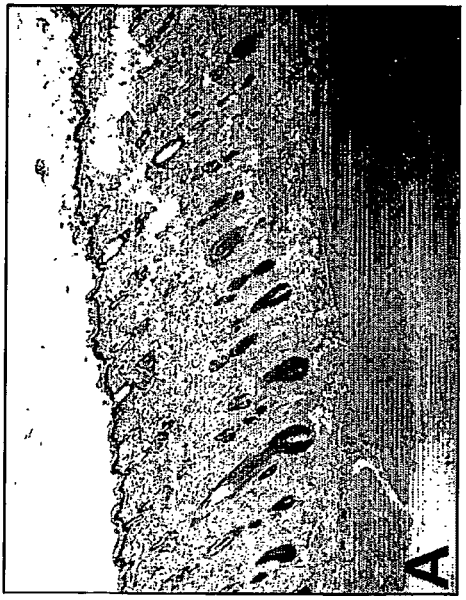
Figure 3:
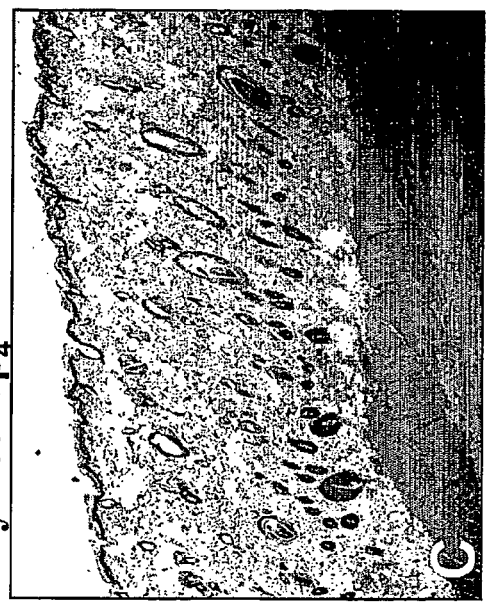

In addition, Example 2 describes experiments that were conducted to directly test the effects of topically applied thymosin β₄ on normal (i.e., unwounded) female rat skin. At the end of the experiment, the animals were sacrificed, tissue sections prepared in 10% buffered formalin, and stained using standard histological stains. As shown in FIGS. 2 and 3, thymnosin β₄ was found to stimulate new hair growth at both day 7 and day 30 after treatment. All other aspects of the skin appeared to be unaffected at thirty days after treatment, with little change in the epidermis or in the thickness of the dermis.

In further experiments detailed in Example 3, athymic nu nu nude female mice were tested to determine whether thymosin β₄ would promote hair growth on their backs. Visible hair growth was observed macroscopically. No enhanced hair growth or other differences were observed in skin treated identically with the control (i.e., hydrogel) without thymnosin β₄.

Figure 5:
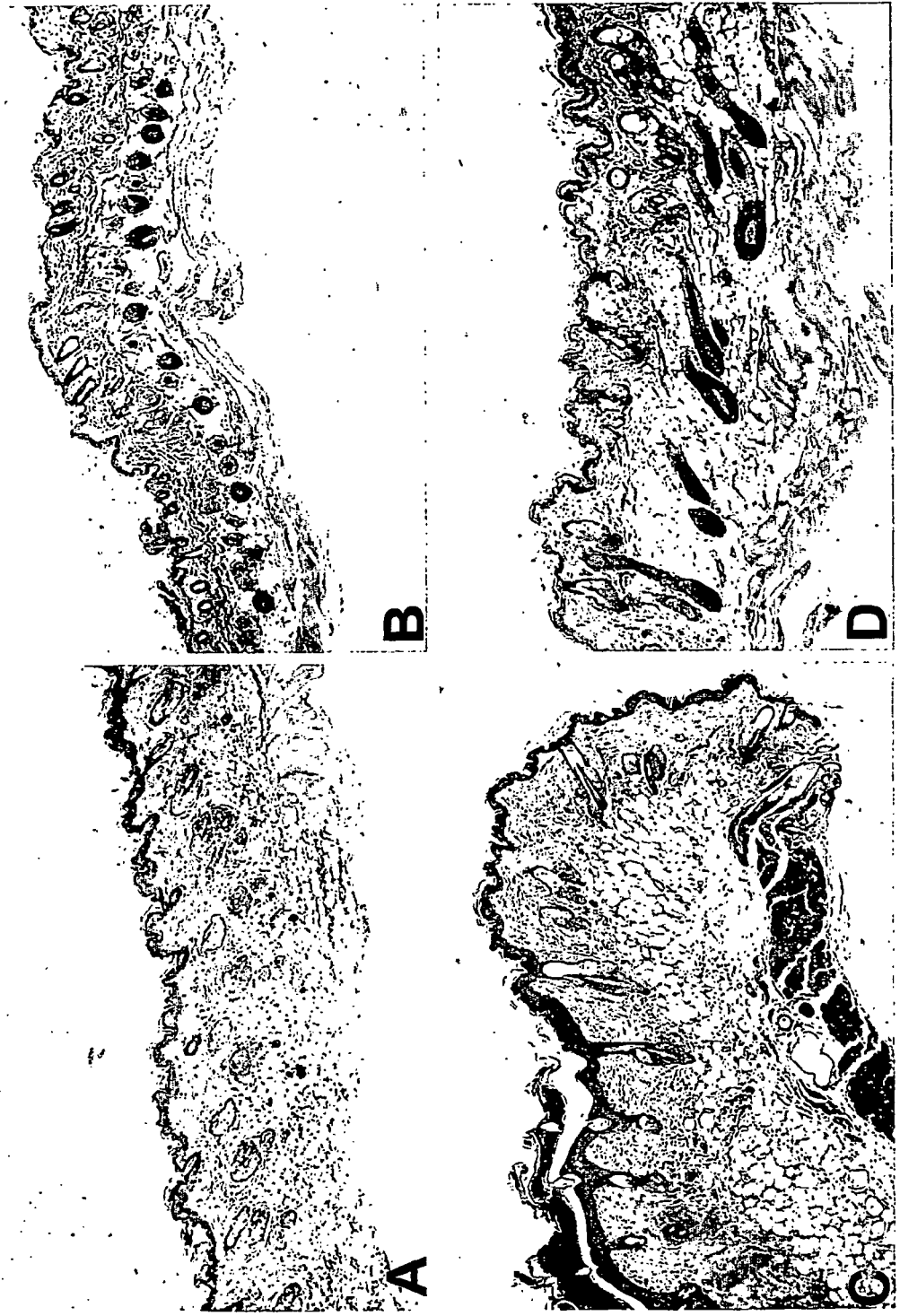
FIGS. 5A-5D are digital images of photomicrographs showing that aged mice treated with thymosin $\beta_4$ exhibit increased follicle development after a 7 day study of treatment with 0.05% thymosin $\beta_4$ in hydrogel.

In addition, the effects of thymosin β₄ in 26 month old aged female BALB/c mice were determined. New follicle development was clearly observed, as shown in FIG. 5. In further experiments with these aged mice, a synthetic fragment of thymosin β₄ containing the seven amino acid sequence T-3 was tested for its ability to stimulate hair growth. The results indicated that this fragment increased hair follicle development over that observed with water alone. Thus, it is contemplated that a fragment of thymosin β₄, including a polypeptide comprising the fragment, will find use in hair regeneration compositions.

The disclosed methods promote hair growth in both aged and nude mice. Generally, the hair is coarser-appearing, and this is evidenced at the histological level by the relative number of larger follicles in the treated skin. When examining the distribution of thymosin β₄ in newly activated hair follicles, one finds that it is expressed in the bulge region, and as the follicles actively grow, it is expressed in a subset of cells that migrate from the bulge region to the bulb area where active hair growth is initiated. Isolated clonogenic hair follicle stem cells produce thymosin β₄. When added exogenously to these cells, increased migration and increased MMP-2 levels are observed. These data demonstrate that thymosin β₄ increases hair follicle growth by activating hair follicle stem cells. Again, the disclosed methods and compositions promote many activities in stem cells that are important for hair growth, including migration, protease production, and differentiation.

As the seven amino acid sequence of T-3 includes an actin-binding domain, other peptides containing actin-binding domains will find use in promoting hair growth. It is also contemplated that homologues of this sequence and fragments of the Tβ4 sequence SEQ ID NO: 1 (for example with conservative and/or non-conservative amino acid changes in the actin-binding domain, or exclusively outside the actin-binding domain) will find use in promoting hair growth. Any conservative change in the amino acid sequence that preserves charge or hydrophobicity, e.g., lysine to arginine, threonine to serine or leucine to arginine, will preserve the activity of an actin-binding domain or fragment containing an actin-binding domain. For example, other actin-binding proteins that contain the sequence of T-3 or residues 17-22 of SEQ ID NO: 1 including, but not limited to various β-thymosins or fragments thereof (e.g., Tβ₄$^{Ala}$, Tβ₄$^{Xen}$, Tβ₉, Tβ₉$^{Met}$, Tβ₁₀, Tβ₁₁, Tβ₁₂, Tβ₁₂$^{perch}$, Tβ$^{sea\ urchin}$, Tβ₁₃ (all of the foregoing containing the T-3 sequence, Leu Lys Lys Thr Glu Thr Gln), as well as Tβ$^{scallop}$ and Tβ₁₄ (containing the sequence Leu Lys Lys Thr Asn Thr Glu)) will find use in the present disclosure. Other examples are peptides containing T-3 (residues 17-23) or residues 17-22 of SEQ ID NO: 1 with 1 to 2 conservative amino acid substitutions to either sequence. Examples of similar actin-binding peptides are those found in Tβ$^{zebrafish}$ (containing the sequence Leu Arg Lys Thr Glu Thr Gln) and Tβ₁₅ (containing the sequence Leu Lys Lys Thr Asn Thr). Thus, virtually any known β-thymosin or fragment thereof contains an actin-binding motif useful in the present disclosure. See Huff et al., "β-Thymosins, small acidic peptides with multiple functions," *Intl. J. Biochem. &Cell Bio.* 33:205-220 (2001) (β-thymosin abbreviations defined and sequences provided therein; some sequences are also duplicated in Table 2). A comparison of these different sequences also provides guidance about amino acid substitutions that can be made in the Tβ4 actin-binding domain while preserving its therapeutic activity. For example, the residues at positions 1, 3 and 4 appear to be highly conserved, and would therefore be less likely candidates for substitution.

Additionally, methods known in the art for enhancing the activity of small peptides are useful in combination with the disclosed sequences that promote hair growth. Such methods may increase the half-life of such peptides in the subject, or increase activity for other reasons. For example, various fusion molecules known in the art may be used. Poly(ethylene glycols) ("PEGs") of various molecular weights, especially including those weighing approximately 3,000 to 9,000 gm/mol, converted to amino-poly(ethylene glycol) ("APEG") can be coupled to short peptides to result in increased activity as described in Kawasaki et al., "Preparation of [Arg-Gly-Asp]-[Amino-poly(ethylene glycol)] hybrids and their inhibitory effect on experimental metastasis," *Chem. Pharm. Bull.* 3373-3375 (1991). Chitosan may also be linked to peptides to result in increased activity as described in Hojo et al., "Preparation of a chitosan hybrid of an antimetastatic laminin-related peptide," *Pharm. Pharmacol. Commun.* 5:277-280 (1999). The same is true for bovine serum albumin, *Staphyloccocal* protein A (see Maeda et al., *J. Biochem.* 115:182-189 (1994)), fibronectin and any normal serum protein. Accordingly, fusion of the actin-binding motifs disclosed herein to other molecules will also result in improved hair growth activity in subjects.

Other strategies for increasing the activity of small peptides can also increase the activity of the sequences described herein for promoting hair growth. Linear or branched polymers of a peptide sequence can increase activity either atone or in combination with fusion molecules. Various approaches are known in the art for enhancing activity by formation of polymers. See, e.g., Kawasaki et al., *Biochem. and BioPhys. Res. Comm.* 174:1159-1162 (1991); Nomizu et al., *Cancer Res.* 53: 3459-3461 (1993); Saiki et al., *Br. J. Cancer* 59:194-197 (1989); Murata et al., *Int. J. Biol. Macromol.* 11:97-99 (1989); Saiki et al., *Cancer Res.* 49:3815-3822 (1989). The activity of amino acid sequences disclosed herein can accordingly be improved by making polymers or copolymers including those sequences and, optionally, fusing those polymers to another molecule. Such structures include: (T-3)$_n$, (T-3)$_n$-APEG, (T-3)$_2$, (Tβ4)$_n$, (T-3)$_m$-(Tβ4)$_n$, (Leu Lys Lys Thr Asn Thr)$_n$, [(Leu Lys Lys Thr Asn Thr)-(Leu Lys Lys Thr Asn Thr Gln)]$_n$, (Leu Lys Lys Thr Asn Thr Gln Glu)", (Leu Lys Lys Thr Asn Thr Glu)$_n$, (T-3)-Cys-Cys-(T-3), Cys-(T-3)$_n$-Cys [cyclized through a disulfide bond], [Ac-(T-3)]$_8$Lys₄Lys₂LysGly-OH, etc. where n represents a number greater than 1, such as a whole number (for example 2) or fractional number (for example 2.5). In particular examples the polymer is a linear polymer with a repeating motif of Leu Lys Lys Thr Asn Thr or Leu Lys Lys Thr Asn Thr Gln, and in some examples n is more than 2 but less than 100, for example 2 to 50 or 2 to 10. The repeating motif can be included in a polypeptide that includes amino acid sequences other than the repeating motif.

Because the disclosures herein isolate and provide the active domain of various peptides, rather than merely a full length, naturally occurring protein such as Tβ4, certain advantages are obtained by the disclosed methods in which shorter peptides are used. Such advantages include facilitating the simpler and more economic synthesis of active peptides that can be shorter than the natural full length protein. Another advantage is that the shorter peptides allow for greater activity by weight with similar activity on a molar basis, and in some instances may have superior penetration or bioavailability at their site of action. The present methods even allow enhanced activity over the natural proteins by, for example, allowing for the use of peptides containing more than one active site.

The following examples are provided in order to demonstrate and further illustrate certain embodiments and aspects of the present disclosure and are not to be construed as limiting the scope thereof.

EXAMPLE 1

Demonstration of Hair Growth in Rats

This Example demonstrates the promotion of hair growth by thymosin β4 in rats. In the course of performing wound healing studies in female rats, a hydrogel formulation containing thymosin β4 was developed. In particular, preparations of 0.05% thymosin β4 were prepared in 0.2% hydrogel (polyacrylic acid, Hawkeye-Jensen, Inc.). This formulation was applied to wounds using a cotton swab as an applicator. The control animal received gel alone.

The test rats were shaved once at the beginning of the experiment to remove as much hair as possible on their backs to allow penetration of the reagent and control vehicle. Six full thickness 8 mm punch wounds were made in the backs of 8 week old Sprague Dawley rats using three rats per data point. Thymosin β4 at a concentration of approximately 25 µg/50 µl in hydrogel was applied to the wounds with a cotton swab on the day of wounding and at 48 hours after wounding. The exact volume applied was estimated but it was applied as a thin smear. The gel was difficult to place exactly in the wound and some adjacent tissue came in contact with the gel. When the wounds were examined visually, increased hair growth around the wound site was clearly observed. The hair growth visually appeared longer and denser than the surrounding hair in other shaved areas of the animal. After 7 days, the animals were sacrificed and tissue sections of the area where the gel was applied were fixed in 10% buffered formalin and stained using methods known in the art (H&E and Masson's trichrome stains, Histoserv, Gaithersburg, Md.). As shown in FIG. 1, histological data indicated that there was an increase in the number of hair follicles observed in the thymosin β4-treated animals, relative to control gel-treated animals and untreated skin.

EXAMPLE 2

Effects of Thymosin β4 on Normal Rats

This Example demonstrates the effects of topically applied thymosin β4 on normal (unwounded) female rat skin. In these experiments, 8 week old female Sprague Dawley rats were utilized. Thymosin β4 was applied on the shaved backs of the animals at a concentration of 0.5 mg/ml in hydrogel three times per week (Monday, Wednesday and Friday). The hair of the animals was observed over 30 days. Some of the animals were sacrificed on day 7 after the initiation of treatment, while others were sacrificed on day 30 after initiation of treatment. Tissue sections were prepared using methods known in the art, as indicated above in Example 1. The tissue section samples were all read and compared on a blind basis by an observer trained in dermatology.

As shown in FIG. 2, thymosin β4 was found to stimulate new hair growth at day 7. Also, as shown in FIG. 3, new hair growth was stimulated by thymosin β4 at 30 days after application. All other aspects of the skin appear unaffected 30 days after treatment with little change in the epidermis or in the thickness of the dermis. No increase in collagen deposition was observed and the number of blood vessels appeared to be unchanged, although some increase in inflammatory cells was observed.

EXAMPLE 3

Effects of Thymosin β4 on Female Mouse Skin

Figure 4:
FIGS. 4A and 4B are digital images of photomicrographs showing an increase in the number of actively growing hair follicles following 30 days of topical treatment of athymic nude mice with thymosin $\beta_4$. An increased number of follicles was also observed relative to a hydrogel control.
Figure 4:
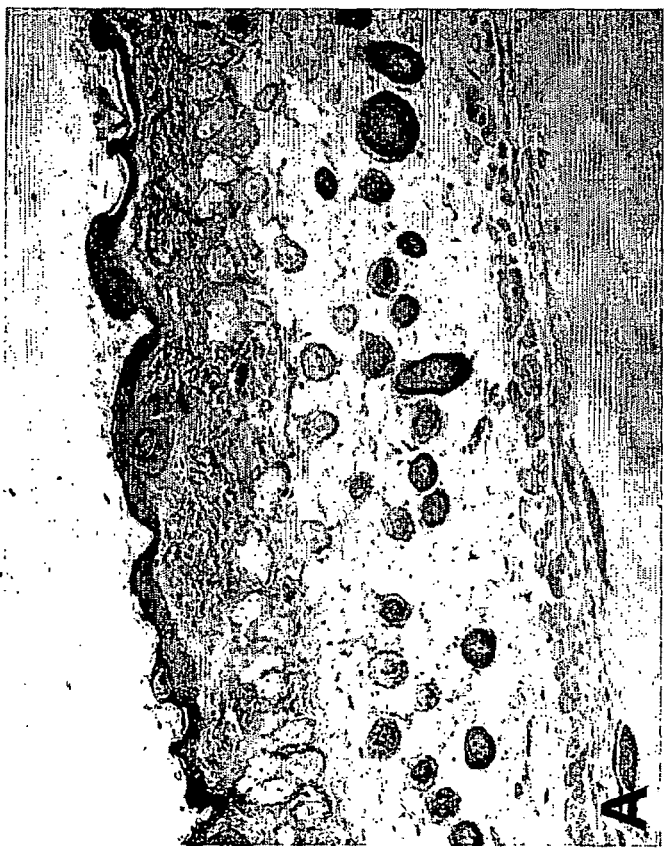

This Example demonstrates the effects of thymosin β4 on the skin of athymic nu nu female mice. Athymic nu nu nude female mice, which lack visible hair in their skin but do have some follicles, were tested to see if thymosin β4 would promote hair growth. After treatment with thymosin β4 three times per week for 35 days (at the same concentration as indicated in the previous Example), visible hair growth was observed macroscopically and increased numbers of new hair follicles were observed by histology. See FIG. 4.

The effects of thymosin β4 were also demonstrated in 26 month old aged female BALB/c mice. These mice are considered highly aged as they are alive beyond the normal mouse life expectancy. These mice exhibit many of the symptoms of old age including cataracts, arthritis, poor wound healing, and thinning hair. The mice were shaved and treated as described above with thymosin β4 at the time of shaving and 48 hours later. At day 7, the skin was harvested and examined histologically, as described above in Example 1. New follicle development was clearly observed, as shown in FIG. 5.

To demonstrate that the T-3 portion of thymosin β4 containing the seven amino acid actin-binding domain at amino acids 17-23 has the activity of the full length Tβ4, the T-3 peptide was applied to the aged mice in the same manner. The T-3 fragment was produced using an automated peptide synthesizer, as is well known in the art.

Figure 6:
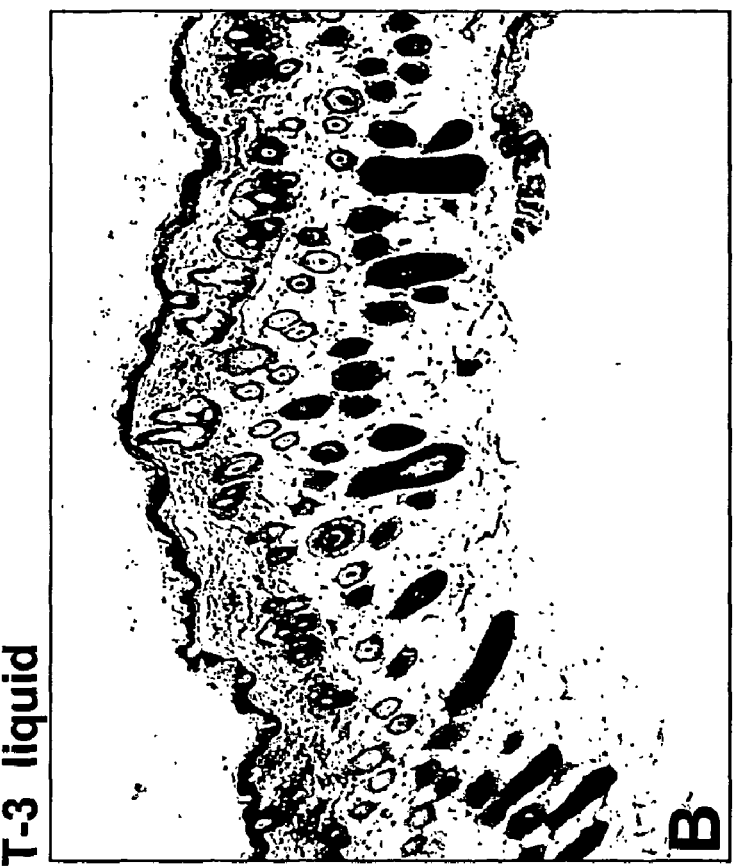
FIGS. 6A and 6B are digital images of photomicrographs of skin samples showing that a 7-amino acid fragment of thymosin $\beta_4$ (amino acids 17-23, i.e., Leu Lys Lys Thr Glu Thr Gln, of SEQ ID NO: 1 which is also referred to herein as "T-3") applied in a water vehicle, stimulates increased hair follicle development in aged mice.
Figure 6:

The synthetic T-3 peptide was applied in a water solution/mixture at a concentration/dose of 5 µg/50 µl. The results (see FIG. 6) indicate that this fragment increased hair follicle development over that observed in the control treatment using water alone. Thus, a fragment of thymosin $\beta_4$ comprising these amino acids is useful in hair regeneration compositions.

EXAMPLE 4

Hair Growth Studies Using Aged Mouse, Nude Mouse and Rat Models

To further demonstrate the effects of thymosin $\beta_4$ on hair growth, 0.05% of the peptide was combined with a hydrogel carrier and applied topically to shaved rats, shaved aged mice (24 to 26 months old), and nude mice every other day.

One study used shaved rats where thymosin $\beta_4$ was applied topically on one side of the shaved area and on the opposing lateral side a control vehicle was applied. After 7 days of treatment, an increased number of hair follicles in the anagen phase was observed in rats treated with thymosin $\beta_4$ (see FIG. 7A). The number of anagen follicles was approximately two-fold greater than in rats treated with the control vehicle alone (see FIG. 7D). The hair appeared longer and thicker than hair growing in untreated areas and the follicles were larger in diameter. The increased number of hairs in the anagen phase was retained with continued tri-weekly treatment over 30 days. However, within 14 days of ceasing treatment, the number of active hair follicles decreased to control levels.

Figure 7:
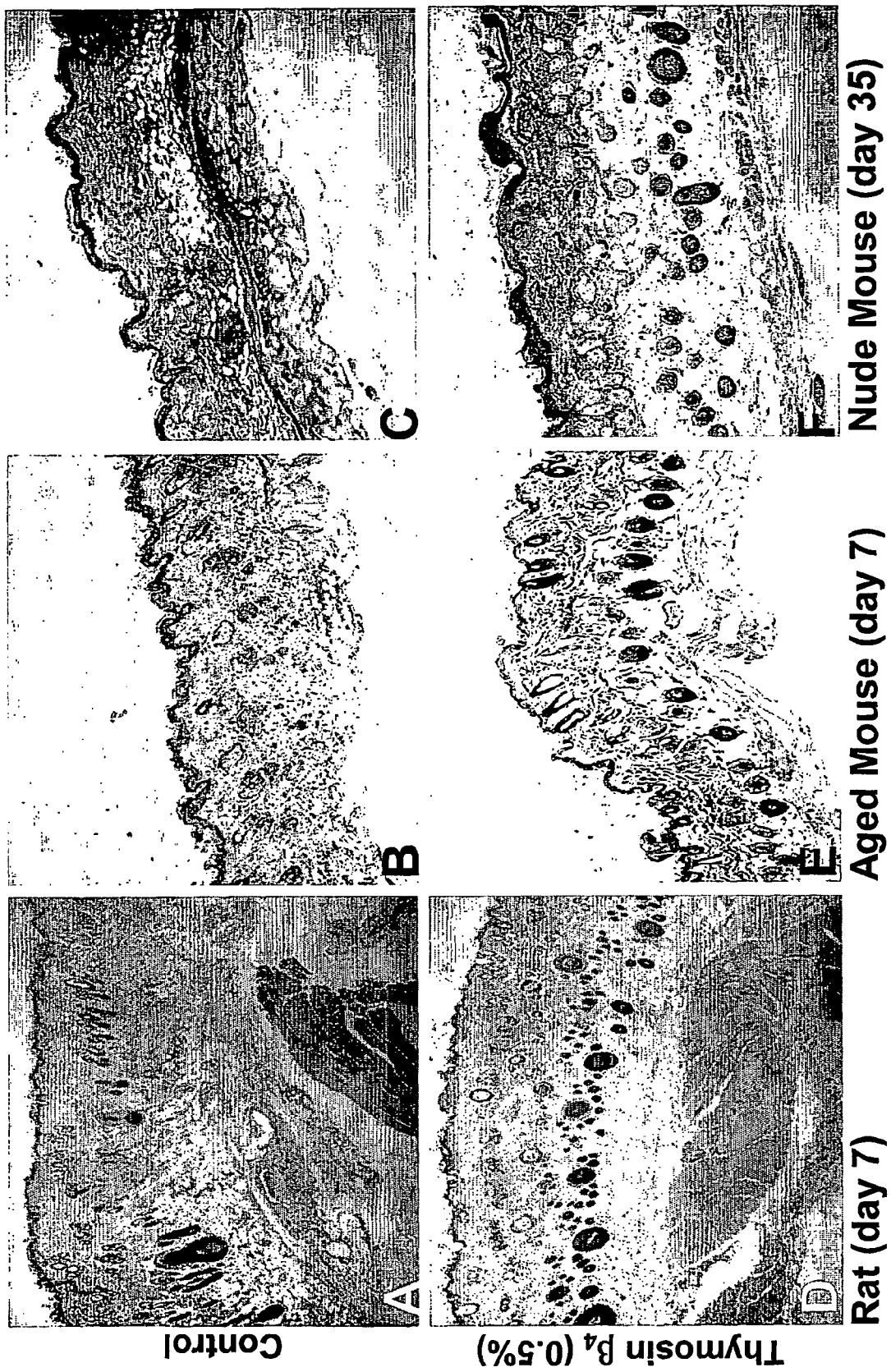
FIGS. 7A-7F are digital images of photomicrographs showing the histological appearance of skin from control and thymosin $\beta_4$-treated animals.

Aged mice (22-26 weeks) showed similar increases in hair follicle growth after 7 days of treatment (see FIGS. 7B, 7E). Treatment of nude mice showed increased hair growth in treated areas at day 7 and at day 35 (see FIGS. 7E, 7F). These data demonstrate that thymosin $\beta_4$ enhances hair growth when applied topically to rat and murine models.

EXAMPLE 5

Migration Assay

Clonogenic keratinocyte migration was studied in a 48-well Boyden chamber using 8 μm pore polycarbonate, PVPF, membranes (Poretics, Livermore, Calif.) coated with 50 μg/ml of rat tail collagen type 1 (BD Biosciences, Bedford, Mass.) diluted in keratinocyte-SFM that contained 72 mM HEPES buffer (Envitrogen, Carlsbad, Calif.). The coated membranes were dried for 2 hrs prior to use. Cultured clonogenic keratinocytes were harvested using trypsin (Invitrogen, Carlsbad, Calif.) and re-suspended in binding medium that contained the following: Keratinocyte-SFM, 1% bovine serum albumin factor-V (Sigma, St. Louis, Mo.), and 25 mM HEPES buffered solution. The bottom chamber was filled with a binding medium that contained either 1 or 100 ng of synthetic T$\beta$4 (FDA) in triplicate. Conditioned fibroblast medium was used as a positive control. Keratinocytes were added to the upper chamber at a concentration of 30,000 cells per well and the assay was incubated at 37° C. with 5% $CO_2$ for 4.5 hrs. The membranes were then fixed and stained with Diff-Quik (VWR). The number of cells that successfully migrated through the pores of the membrane were quantitated by counting cells in 3 random areas of each well and averaging the cell number counted. Cell counts were done at 10× using a Nikon Optiphot-2 microscope. This assay was repeated twice.

Clonogenic Keratinocytes Migrate Toward Thymosin $\beta_4$ In Vitro

T$\beta$4 has been previously shown to promote endothelial cell migration. Malinda et al. (1997). Cultured clonogenic keratinocyte migration in the Boyden chamber assays showed a response to T$\beta$4 after 4.5 hrs. Cell migration with T$\beta$4 present was increased almost 2 fold ($p \leq 0.0006$) over migration in the presence of binding medium alone (see Table 1). The effect of the peptide on cell migration was greatest at 1 ng per ml and showed a decrease in migration at the higher T$\beta$4 concentration.

TABLE 1

Clonogenic keratinocyte migration increases in the presence of T$\beta$4.

| (cells/field) | Negative Control | T$\beta$4 (1 ng) | T$\beta$4 (100 ng) | Fibroblast Conditioned Med. |
|---|---|---|---|---|
| Average | 69 ± 7.12 | 113.3 ± 5.5 | 79.3 ± 6.6 | 164.3 ± 11.4 |
| P value | | $\leq 0.0006$ | $\leq 0.200$ | $\leq 0.0001$ |

SEM was calculated for each value in Table 1.

EXAMPLE 6

Demonstration of Thymosin $\beta_4$ Protein Activity During Hair Growth

Depilation was used to induce the hair growth cycle in resting follicles, as described in Paus et al., "Telogen skin contains an inhibitor of hair growth," *Br. J. Dermiatol.* 122: 777-784 (1990). Briefly, the back skin of 8 week-old female C57/BL6 mice at telogen phase (as identified by their pink skin color) was depilated using a Hair Remover Wax Strip kit (Del Laboratories, Farmingdale, N.Y.), leading to synchronized development of anagen hair follicles. Skin tissue samples were collected at day 0 (unmanipulated skin—telogen), day 4 postdepilation (early anagen) and day 9 postdepilation (late anagen); 5 mice per time point. The samples were fixed in 4% paraformaldehyde and embedded in paraffin.

Thymosin $\beta_4$ Protein Expression by a Subset of Hair Follicle Cells

Figure 8:
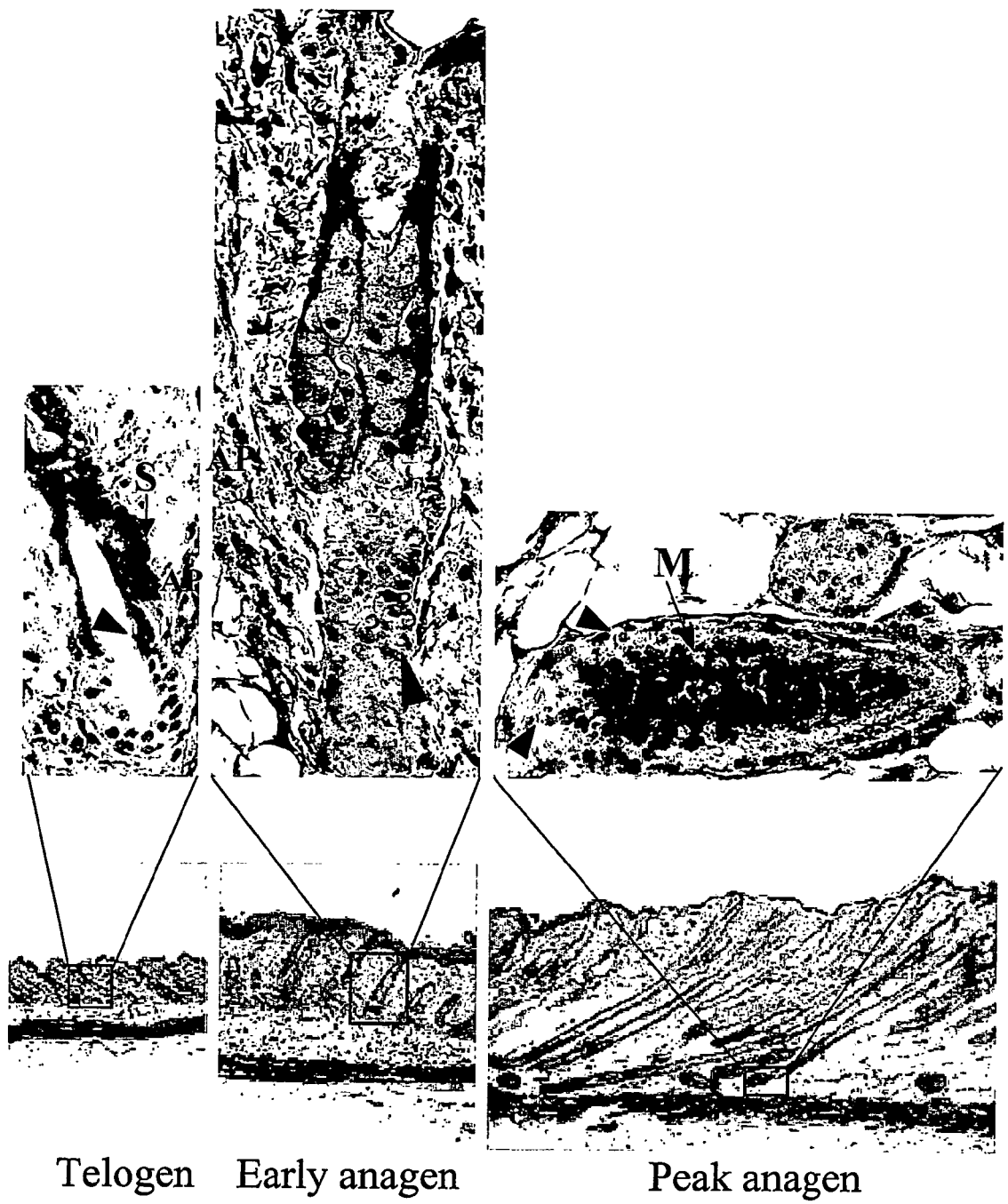
FIGS. 8A-8C are digital images of photomicrographs showing the histological appearance of normal mouse skin after a depilation-induced hair growth cycle and immunological localization of thymosin $\beta_4$ expressing cells. (S=sebaceous gland; M=hair matrix; AP=arrector pili muscle; Arrowheads denote location of bulge region and thymosin $\beta_4$-positively stained cells.)

The spatial and temporal pattern of endogenous thymosin $\beta_4$ expression in hair follicles during the depilation-induced, synchronized adult hair cycling in C57/BL6 mice was demonstrated. This was done to correlate the observed effects of thymosin $\beta_4$ administration with functional involvement of endogenous thymosin $\beta_4$ in hair growth. One day after depilation, low levels of thymosin $\beta_4$ protein were observed in follicles at the telogen (resting) phase (FIG. 8). In these follicles, thymosin $\beta_4$ expression was confined to a small number of cells residing in the bulge region, with no thymosin $\beta_4$ detected in the upper or lower follicle. The sebaceous gland was stained at all stages, possibly due to non-specific absorption of anti-thymosin $\beta_4$ antibody.

Hair follicle transition to the early anagen phase (day 4 after depilation) was associated with an increased number of thymosin $\beta_4$-expressing cells in the bulge region (FIG. 8).

Moreover, some thymosin $\beta_4$-positively stained cells were detected in the lower part of the follicle, between the bulge and bulb area. At late-anagen (day 8 after depilation), significant numbers of the cells located in the lower follicle (including the matrix and outer root sheath) expressed thymosin $\beta_4$. These data show that the temporal and spatial distribution of thymosin $\beta_4$-expressing cells was similar to the pattern proposed for the location of hair follicle stem cells (see Taylor et al., *Cell* 102:453-461 (2000), and Oshima et al., *Cell* 104: 233-245 (2001)). With the initiation of hair growth, thymosin $\beta_4$-positive cells are observed outside of the bulge region near the bulb area, where they would be migrating from the bulge region.

EXAMPLE 7

Isolation of Clonogenic Keratinocytes (Hair Follicle Stem Cells) from Rat Vibrissae Clonogenic keratinocytes were isolated from rat vibrissa follicles as described in Kobayashi et al., "Segregation of keratinocyte colony-forming cells in the bulge region of the rat vibrissa," *Proc. Natl. Acad. Sci. USA* 90:7391-7395 (1993), with some modifications. Briefly, Fisher 344 rats were sacrificed by carbon dioxide asphyxiation. The upper lip containing the vibrissal pad was cut and its inner surface was exposed. The vibrissa follicles were dissected under a binocular microscope, plucked from the pad and then kept in a sterile culture medium. A fragment containing the bulge region of the follicle was cut off and incubated for 30 min in collagenase/dispase solution (1 mg/ml; Roche Molecular Biochemicals, Quebec, Canada) at 37° C. The epithelial core was then detached from the collagen capsule and further incubated in 0.05% trypsin solution (30 min, 37° C.) to facilitate the dissociation of epithelial cells. Isolated cells were cultured in Keratinocyte-SFM medium, supplemented with EGF, Bovine pituitary extract (Invitrogen, Carlsbad, Calif.) and 10% FCS (Hyclone, Logan, Utah).

Cultured Rat Vibrissa Clonogenic Keratinocytes Express Thymosin $\beta_4$

Figure 9:
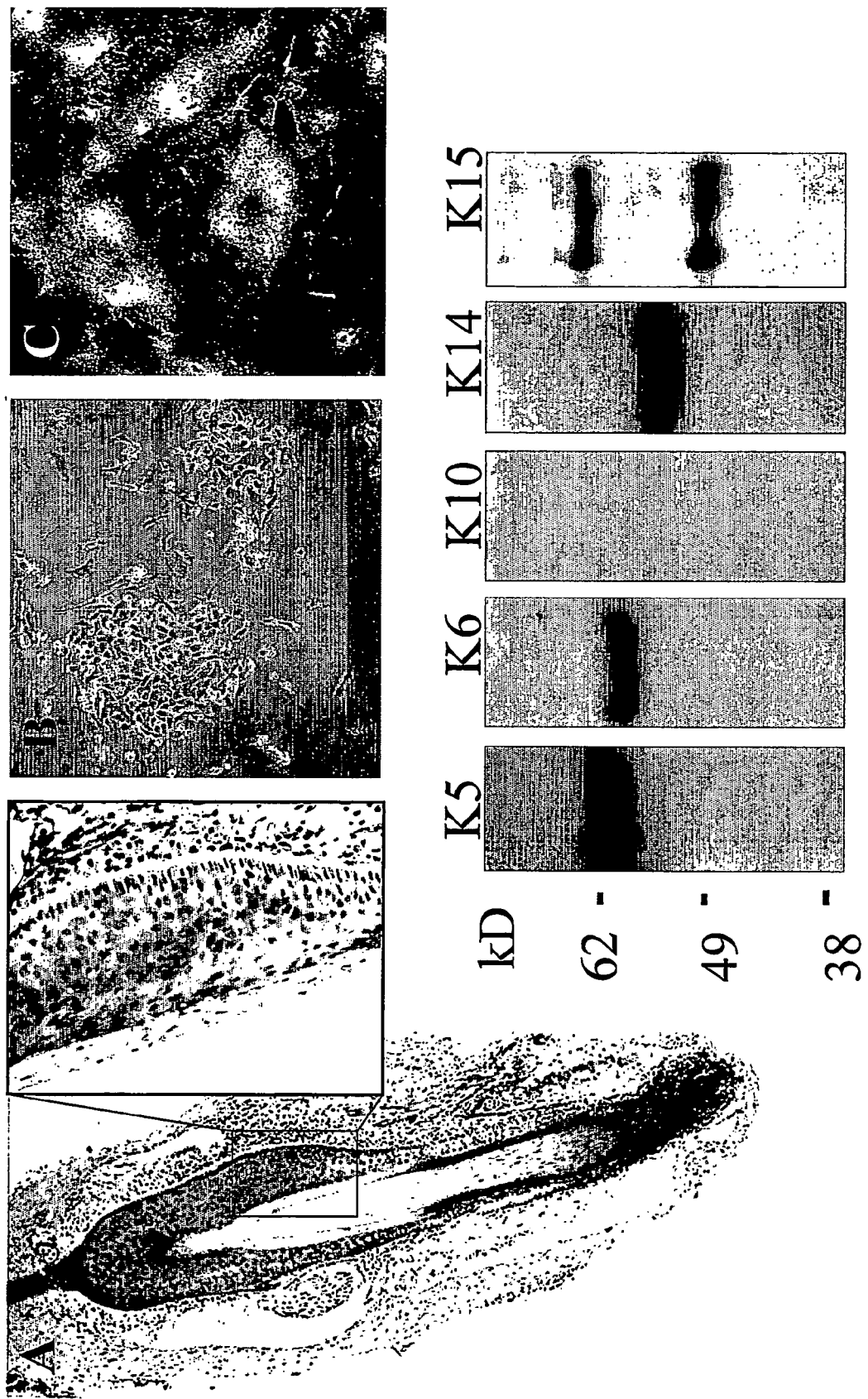
FIGS. 9A-9C are digital images on photomicrographs showing the isolation, culture, and expression of various keratins and thymosin $\beta_4$ by clonogenic stem cells from rat vibrissae.
FIG. 9D is a Western blot of clonogenic stein cells with various keratin antibodies showing the pattern of keratin expression by isolated stem cells. Note the absence of expression of keratin 10 (K10), an early marker of terminal differentiation, and the presence of K5, K14 and K15 characteristic for bulge-derived stem cells.

Rat vibrissae follicle keratinocytes from the bulge region expressed thymosin $\beta_4$. Previously, hair follicle stem cells residing in the bulge region have been identified as keratinocytes with a high in vitro proliferative potential. Although hair follicle stem cells are not fully characterized in terms of specific markers, they express preferentially cytokeratin 15 (K15). Clonogenic keratinocytes isolated from the rat vibrissa bulge region (FIGS. 9A, 9B) showed that the isolated cells are highly clonogenic (FIG. 9C). These cells express stem cell marker K15 but are negative for cytokeratin 10 (K10), a known early marker of terminal keratinocyte differentiation (FIGS. 9A, 9D). Moreover, when cultured in vitro, these cells were able to move with an average velocity of 26 μm/hour. These characteristics support the conclusion that the cell population obtained by these methods represents the immediate progeny of hair follicle stem cells. These cells expressed thymosin $\beta_4$ after 3-4 days of culturing in vitro (FIG. 9C).

Figure 10:
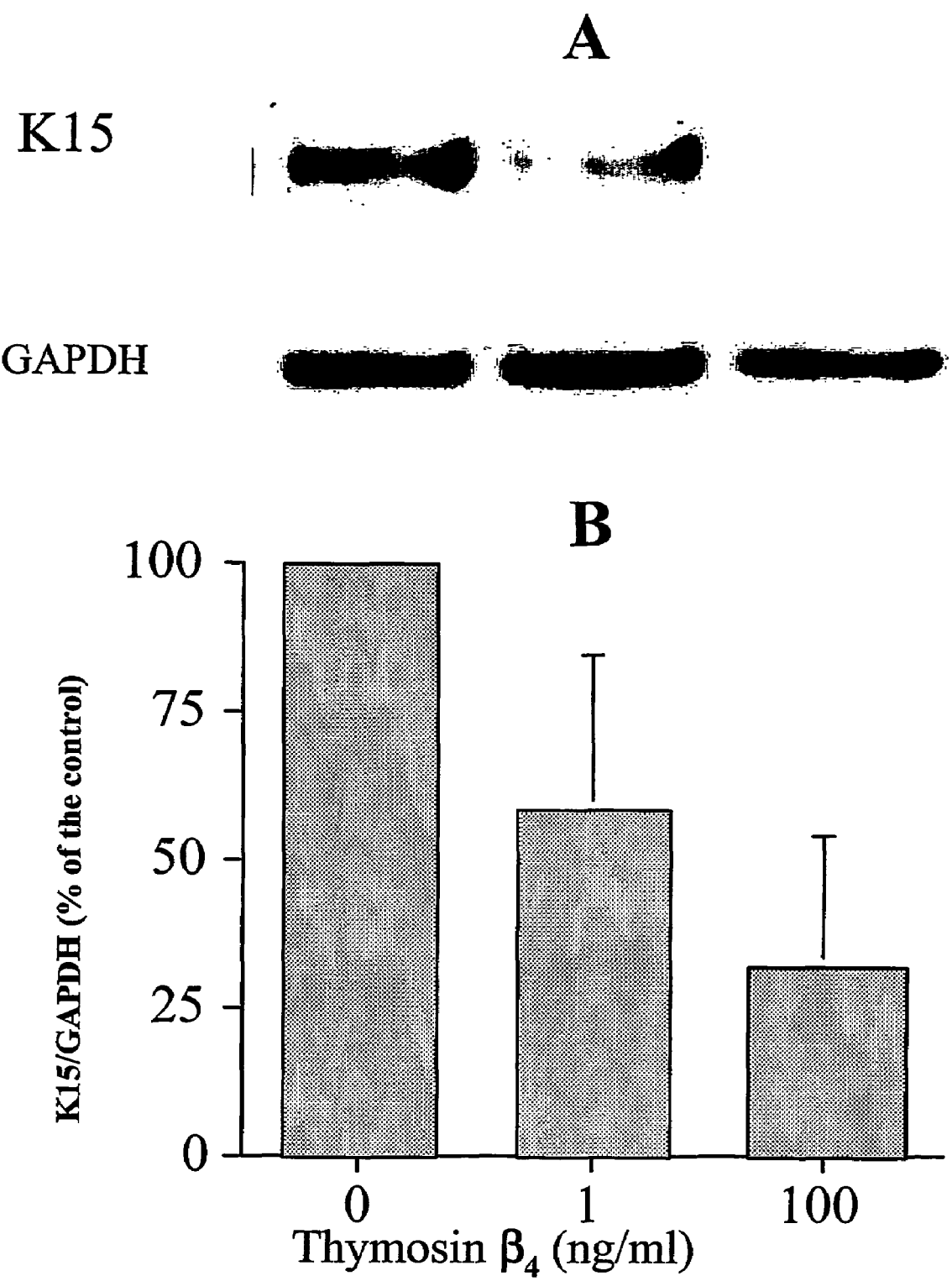
FIGS. 10A and 10B are blots and a graph showing that exogenous thymosin $\beta_4$ decreases keratin 15 mRNA expression by clonogenic rat vibrissae stem cells. Northern analysis and quantitation of the same are also shown. The cells were depleted from serum for 16 hours and then cultured for 6 hours in the absence or presence of different concentrations of thymosin $\beta_4$. Following this treatment cells were lysed with RIPA buffer, and lysates were imunnobloted with anti-K15 antibody (FIG. 1A, upper panel). The same membranes were re-probed with anti-GAPDH antibody (FIG. 10A, lower panel), and the results were normalized by densitometry (FIG. 10B). Decrease in the expression of the stem cell marker K 15 suggests that thymosin $\beta_4$ contributes to hair growth through promotion of hair follicle stem cell differentiation.

Interestingly, treatment of the clonogenic keratinocytes with exogenous thymosin $\beta_4$ causes a dose-dependent decrease in the levels of K15 (FIG. 10), suggesting that thymosin $\beta_4$ is important for early stem cell differentiation (i.e., transition to the TA phenotype). No effect on stem cell proliferation by thymosin $\beta_4$ was found. These data define the cells isolated from rat vibrissa as clonogenic keratinocytes that produce thymosin $\beta_4$.

EXAMPLE 8

Clonogenic Keratinocytes Produce Increased MMP-2 in the Presence of Thymosin $\beta_4$ It was previously proposed that extracellular matrix degradation is a necessary step during normal appendageal development. The effect of thymosin $\beta_4$ on the activity of matrix metalloproteinases (MMPs) was demonstrated in this Example.

Figure 11:
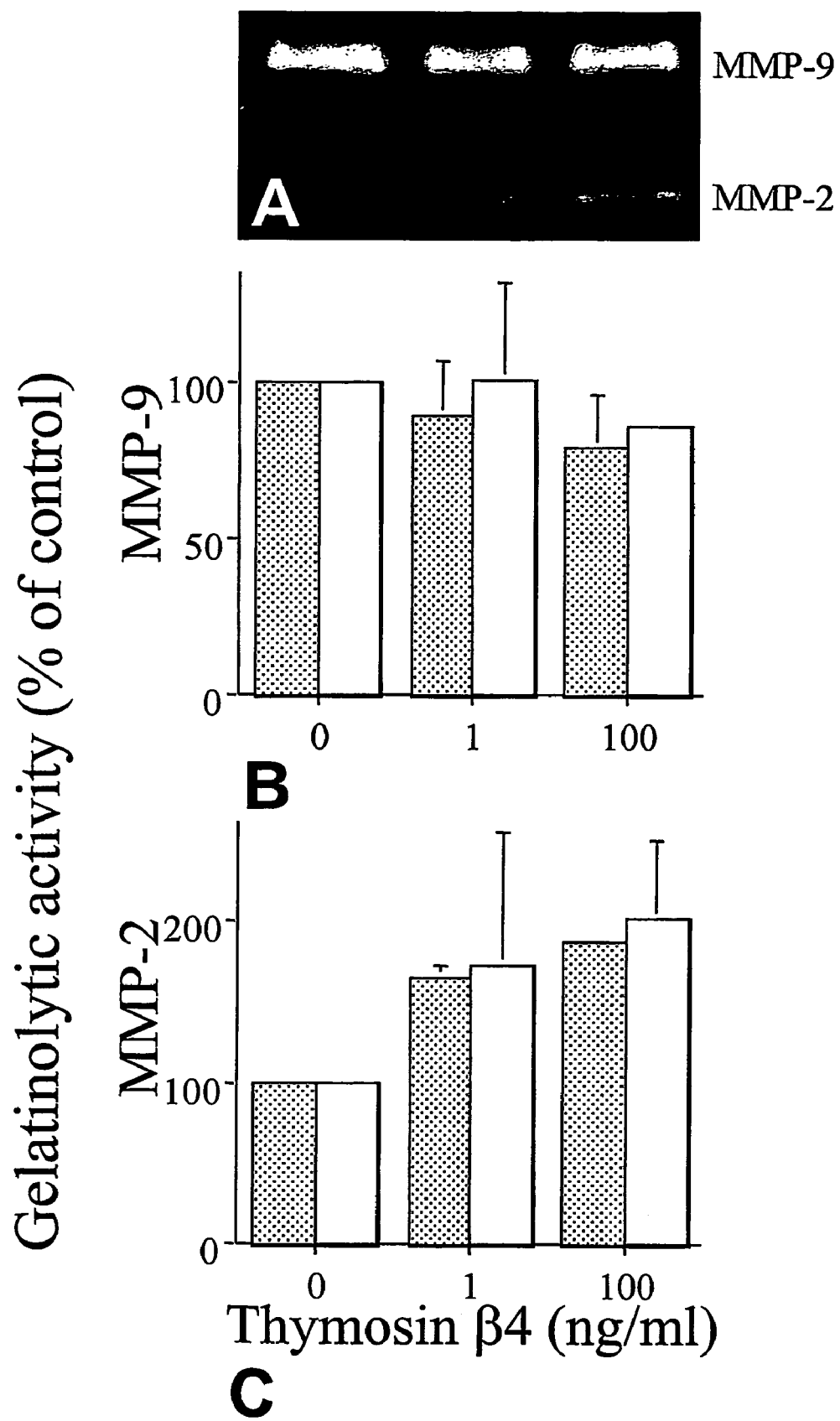
FIGS. 11A-11C are a blot and graphs showing that exogenous thymosin $\beta_4$ increases MM-2 levels but has no effect on MMP-9 levels in clonogenic stem cells. Zymographic analysis and quantitation are also shown. Dotted bars represent cell lysates and filled bars represent the condition medium.

Treatment of clonogenic bulge region-derived stem cells with exogenous thymosin $\beta_4$ caused a dose-dependent increase in the levels of secreted and cell-derived MMP-2 while no significant effect on MMP-9 levels was observed (FIG. 11). These data demonstrate that thymosin $\beta_4$ activates MMP-2 activity, which is important in the escape of stem cells from the bulge region and facilitates their migration to the bulb region.

EXAMPLE 9

Promotion of Hair Growth in Humans

One skilled in the art will readily recognize that the treatments described above can easily be adapted for treating alopecia in humans. Any pharmaceutically suitable carrier, especially those appropriate for topical applications, can be used as a vehicle for administering a peptide containing T$\beta$4, T-3, a fragment of T$\beta$4 that includes an actin-binding sequence, any other actin-binding peptide(s) or mixtures thereof in a therapeutically effective amount. Such peptides can also be applied neat with no vehicle. If a carrier is used, the peptide(s) can be present in any effective amount, but is usually applied in a mixture containing between 0.001% and 50% of the peptide or mixture of peptides. More preferably, the pharmaceutically suitable carrier contains 0.01-5% of the peptide or peptide mixture. The treatment can include one or more doses applied topically to an area locally affected by alopecia. Multiple doses in certain embodiments are applied daily, every other day, one or more times per week, biweekly or monthly. Topical doses can be applied in a lotion, gel, spray, or any other convenient form.

EXAMPLE 10

Identification of Actin-Binding Motifs

Using naturally occurring thymosin $\beta_4$, proteolytic fragments, and synthetic peptides, a 6- or 7-amino acid actin-binding motif of thymosin $\beta_4$ was found to be essential for the observed angiogenic activity, which in turn facilitates the promotion of hair growth. Migration assays with human umbilical vein endothelial cells and vessel sprouting assays using chick aortic arches show that thymosin $\beta_4$ and the actin-binding motif of the peptide display near identical activity at approximately 50 nM, while peptides lacking any portion of an actin motif were inactive. The adhesion and sprouting activity of thymosin $\beta_4$ was inhibited with the addition of 5-50 nM soluble actin. This demonstrates that the actin-binding motif of thymosin $\beta_4$ is an essential site for its angiogenic activity. The data further suggests that cell surface actin may serve as the receptor for thymosin $\beta_4$.

The methods disclosed herein were used to identify actin-binding motifs in several peptides and such methods can readily be used to identify actin-binding motifs in other peptides for promoting hair growth.

Peptides and fragments—Synthetic thymosin $\beta_4$ was provided by RegeneRx, Inc., Bethesda, Md. The following peptide fragments of thymosin $\beta_4$ were synthesized using conventional methods: $T\beta_4^{1-15}$ (i.e., the first 15 amino acid residues of SEQ ID NO: 1), $T\beta_4^{10-28}$ (i.e., amino acid residues 10-28 of SEQ ID NO: 1), $T\beta_4^{20-43}$ (i.e., amino acid residues 20-43 of SEQ ID NO: 1), $T\beta_{15}^{13-23}$ (i.e., amino acid residues 13-23 of SEQ ID NO: 1), $T\beta_4^{17-23}$ (i.e., amino acid residues 17-23 of SEQ ID NO: 1, also referred to as T-3), $T\beta_4^{19-21}$ (i.e., amino acid residues 19-26 of SEQ ID NO: 1), and $T\beta_4^{13-19}$ (i.e., amino acid residues 13-19 of SEQ ID NO: 1). Naturally occurring $\beta$-thymosins, thymosin $\beta_4$-sulfoxide, and proteolytic peptide fragments (i.e., the 7 peptides in the first group of Table 2) were prepared as previously described in Huff et al., *Anal. Chim. Acta* 352:239-248 (1997); Huff et al., *Eur. J. Biochem.* 230:650-657 (1995). All peptides were dissolved in phosphate-buffered saline (PBS) and stored in aliquots at −70° C.

Cells—HUVECs were isolated and used at passages 2-5. Grant et al., *J. Cell Sci.* 108:3685-3694 (1995). The cells were cultured in RPMI 1640 (Invitrogen, Carlsbad, Calif.) supplemented with 20% bovine calf serum (Hyclone Laboratories, Logan, Utah), 200 µg/ml of endothelial cell growth supplement (ECGS) (Collaborative Biomedical Products, Bedford, Mass.), 0.8 U/ml heparin sodium (Fisher Scientific, Pittsburgh, Pa.), penicillin/streptomycin (Invitrogen, Carlsbad, Calif.), 10 µg/ml gentamycin (Invitrogen, Carlsbad, Calif.), and 1% fungizone (Invitrogen, Carlsbad, Calif.).

Cell adhesion—In order to determine which ions are needed for HUVEC adhesion, Laminin-1 peptide (25 ng in 50 µl) and two test concentrations of $T\beta_4$ (100 ng and 500 ng in 50 µl) in 0.1 M carbonate buffer, pH 9.4, were bound to the bottom of U-bottom 96-well plates overnight at 4° C. Wells were then washed twice with PBS and blocked with 150 µl of 3% BSA in PBS (Sigma Chemical Co., St. Louis, Mo.) at room temperature for 30 min. The wells were washed again and 50,000 HUVECs in 50 µl of serum-free medium that contained the indicated salts (1 mM $Ca_2^+$, 0.5 mM $Mg_2^+$ and 0.5 mM $Mn_2^+$) either individually or in combination were added to each well. The HUVECs used in this study were serum-starved for 2 hr prior to use. The plate was incubated for 45 min at 37° C. Cells that did not attach were gently removed with two PBS washes. The remaining cells were stained with 0.2% crystal violet in 20% methanol, washed in water to remove excess stain, dried overnight at 37° C., and lysed with 10% SDS for 10 min, and the plate OD was read at 600 nm. (Molecular Devices precision microplate reader). Each condition was assayed in triplicate, and the assay was repeated three times.

Boyden chamber assay—HUVEC migration assays were conducted in a 48-well micro-chemotaxis chamber (Neuro Probe Inc., Cabin John, Md.) as previously described in Salcedo et al., *J. Immunol.* 166:7571-7578 (2001). Briefly, PVP-free polycarbonate membranes with 8 µm pores were coated with 50 µg/ml of rat tail collagen (BD Biosciences, Bedford, Mass.) in RPMI 1640 that contained 25 mM HEPES (Invitrogen, Carlsbad, Calif.) at 4° C. overnight. The membranes were dried at least 1 hr prior to use. HUVECs were serum-starved for 2 hr, harvested using Versene (Invitrogen, Carlsbad, Calif.), and resuspended in binding medium that contained RPMI 1640 with 1% BSA and 25 mM HEPES. The lower wells of the chamber were loaded with 1, 10, 100, and 1000 ng/ml of thymosin $\beta_4$ or peptide fragments that were diluted in binding medium. Basic fibroblast growth factor (bFGF) (200 ng/ml) was used as a positive control. Cells were added to the upper portion of the chamber at a concentration of 50,000 cells per well. The chambers were incubated at 37° C. for 4 hr. The filters were fixed and stained using Diff-Quik (VWR, Bridgeport, N.J.). The cells that successfully migrated through the pores of the membrane were manually quantitated using a CK-2 Olympus microscope at 10× magnification. Each condition was assayed in triplicate, and the assay was repeated twice.

Chick aortic arch assay—The aortic arch of 13-day-old chick embryos was removed and placed in RPMI 1640. After removal of surrounding connective tissue, transverse sections of the arch were made (1 mm). The resulting aortic rings were carefully attached to the bottom of a 48-well plate, one ring per well, with 20-30 µl of Matrigel (Collaborative Biomedical Products). The rings were placed so that the lumen of each ring could be seen. More Matrigel was added onto the top of the rings to seal them in place. A 100 µl volume of human endothelial—SFM basal growth medium (Invitrogen) containing 1% penicillin streptomycin was added to each well. Thymosin $\beta_4$, peptide fragments, and exogenous actin (Sigma Chemical Co.) were added to wells in serum-free medium, bringing the final volume of each well to 400 µl. ECGS (200 µg/ml) was used as a positive control. The plates were incubated for 24 hr at 37° C. Rings were fixed and stained with Diff-Quik solution II. Sprouting was scored in a blind assessment by an observer using 10× magnification on an Olympus microscope. Six wells were used for each condition tested, and each assay was done three times.

Actin-mediated HUVEC cell adhesion to thymosin $\beta_4$

Manganese was found to be required for cell adhesion to thymosin $\beta_4$ and it was used in all subsequent adhesion assays.

Since thymosin $\beta_4$ contains an actin-binding domain, actin was added to the cell adhesion assay. This showed that soluble actin blocked adhesion to thymosin $\beta_4$. In a control, soluble actin had no effect on laminin-1-mediated adhesion. These data demonstrate that actin can block thymosin $\beta_4$-mediated adhesion and suggest that the actin-binding site on thymosin $\beta_4$ is important in cell binding to thymosin $\beta_4$. The data also suggest that actin may function as a cell surface receptor for thymosin $\beta_4$.

Actin Blocks Aortic Ring Vessel Sprouting in the Presence of Thymosin $\beta_4$

Thymosin $\beta_4$ promoted sprouting using an embryonic chick aortic ring model. Actin was shown to have angiogenic activity in this model system. Neither thymosin $\beta_4$ nor actin were as active as the ECGS positive control in promoting sprouting. Thymosin $\beta_4$-mediated sprouting was significantly inhibited by the addition of exogenous actin. The effect of exogenous actin on thymosin $\beta_4$-mediated angiogenesis is specific since exogenous actin did not inhibit ECGS-mediated vessel sprouting. Some increase is observed in sprouting when actin and ECGS are added together. These data demonstrate that thymosin $\beta_4$ promotes angiogenesis ex vivo and that exogenous actin blocks this activity. Hence it is believed that thymosin $\beta_4$ acts by binding to actin on the endothelial cell surface.

Identification of the Actin-Binding Domain on Thymosin $\beta_4$ for its Angiogenic Activity Various synthetic peptides and proteolytic fragments of thymosin $\beta_4$ were used to determine the active site on T$\beta$4 for endothelial cell migration and vessel sprouting, the processes that are at least in part responsible for enhancing hair growth by the methods disclosed herein. Both synthetic and naturally occurring thymosin $\beta_4$ were active in both assays (Table 2 and data not shown). Thymosin $\beta_4$-sulfoxide was also active. Synthetic peptides and proteolytic fragments containing either the carboxy terminal part or all of the actin-binding sequence ($T\beta_4^{1-26}$, $T\beta_4^{13-23}$, $T\beta_4^{7-43}$, $T\beta_4^{13-43}$, $T\beta_4^{10-28}$, $T\beta_4^{20-43}$, and $T\beta_4^{17-23}$) were generally highly active in the assays. In contrast, synthetic peptides and proteolytic fragments lacking the actin-binding sequence ($T\beta_4^{1-6}$ and $T\beta_4^{13-19}$) were inactive with $T\beta_4^{1-15}$ showing very weak activity in only the sprouting assay. The smallest active synthetic peptide, $T\beta_4^{17-23}$, contained 7 amino acids and was fully active for migration and sprouting (Table 2; previously and in data not shown, it was found that amino acid residues 17-22 of SEQ ID NO: 1 promotes endothelial cell migration). All other members of the β-thymosins ($\beta_4$-sulfoxide, $\beta_4^{Ala}$, $\beta_9$, and $\beta_{10}$) with a conserved actin-binding domain, i.e., amino acid residues 17-22 of SEQ ID NO: 1, were also active (Table 2). The actin-binding domain of thymosin $\beta_{15}$ is contained within amino acids 13-23 was active in the sprouting assay. These data demonstrate that the actin-binding site contained within thymosin $\beta_4$ has a common physiological activity. It is therefore believed that these and other related family members with sequence homology have this activity important to promoting hair growth.

correlates with in vivo activity, the foregoing results indicate which peptides will find use in promoting hair growth.

EXAMPLE 11

Western Blot Analysis and Immunochemistry

In the foregoing examples, Western Blot Analysis was performed in the following manner. Cells were lysed by the addition of RIPA buffer, and samples of cell lysates normalized for equal protein were separated on the 4-12% Bis-Tris NuPAGE gel (Invitrogen, Carlsbad, Calif.). Proteins were transferred to a nitrocellulose membrane (Invitrogen, Carlsbad, Calif.) and were detected using polyclonal antibodies active against mouse keratins 1, 5, 6, 10, 14, 15 (Covance Research Products, Richmond, Calif.). The same membranes were re-probed with anti-GAPDH antibody (Research Diagnostics, Flanders, N.J.), and results were normalized by densitometry, using NIH Image Software.

Immunohistochemical stainings were performed on 5 μm paraffin sections using a polyclonal rabbit antibody raised

TABLE 2

Summary of studies on proteolytic and synthetic peptide fragments of Tβ4

| | Peptide | 1 | 5 | 10 | 15 | 20 | 25 | 30 | 35 | 40 | Migration | Sprouting |
|---|---|---|---|---|---|---|---|---|---|---|---|---|
| Group 1 | $T\beta_4$ | acSDKP | DMAEI | EKFDK | SK<u>LKK</u> | <u>TETQE</u> | KNPLP | SKETI | EQEKQ | AGES | ++ | ++ |
| | $T\beta_4^{1-8}$ | acSDKP | DM | | | | | | | | n.t. | − |
| | $T\beta_4^{1-28}$ | acSDKP | DMAEI | EKFDK | SK<u>LKK</u> | <u>TETQE</u> | KN | | | | n.t. | +/− |
| | $T\beta_4^{18-28}$ | | | DK | SK<u>LKK</u> | <u>TETQ</u> | | | | | + | ++ |
| | $T\beta_4^{7-43}$ | | AEI | EKFDK | SK<u>LKK</u> | <u>TETQE</u> | KNPLP | SKETI | EQEKQ | AGES | ++ | ++ |
| | $T\beta_4^{13-43}$ | | | DK | SK<u>LKK</u> | <u>TETQE</u> | KNPLP | SKETI | EQEKQ | AGES | + | +/− |
| | $T\beta_4^{27-48}$ | | | | | | PLP | SKETI | EQEKQ | AGES | + | +/− |
| Group 2 | $T\beta_4^{1-16}$ | acSDKP | DMAEI | EKFDK | S | | | | | | − | +/− |
| | $T\beta_4^{10-28}$ | | | EKFDK | SK<u>LKK</u> | <u>TETQE</u> | KNPL | | | | + | ++ |
| | $T\beta_4^{20-48}$ | | | | | <u>TETQE</u> | KNPLP | SKETI | EQEKQ | AGES | ++ | + |
| Group 3 | $T\beta_4^{17-28}$ | | | | <u>LKK</u> | <u>TETQ</u> | | | | | n.t. | ++ |
| | $T\beta_4^{18-28}$ | | | | <u>K</u> | <u>TETQE</u> | KN | | | | n.t. | + |
| | $T\beta_4^{18-19}$ | | | DK | SK<u>LKK</u> | | | | | | n.t. | − |
| | $T\beta_{15}^{18-28}$ | | | DK | SK<u>LKK</u> | TNTE | | | | | n.t. | + |
| Group 4 | $T\beta_4^{(O)}$ | acSDKP | DMAEI | EKFDK | SK<u>LKK</u> | <u>TETQE</u> | KNPLP | SKETI | EQEKQ | AGES | ++ | ++ |
| | $T\beta_4^{Ala}$ | acADKP | DMAEI | EKFDK | SK<u>LKK</u> | <u>TETQE</u> | KNPLP | SKETI | EQEKQ | AGES | n.t. | + |
| | $T\beta_9$ | acADKP | DLGEI | NSFDK | AK<u>LKK</u> | <u>TETQE</u> | KNTLP | TKETI | EQEKQ | AK | ++ | + |
| | $T\beta_{10}$ | acADKP | DMGEI | ASFDK | AK<u>LKK</u> | <u>TETQE</u> | KNTLP | TKETI | EQEKR | SEIS | ++ | + |

Legend for Table 2:

The actin-binding motif is underlined.

Scoring of activity for each assay: n.t. = not tested, − = no activity, +/− = low activity, + = active, and ++ = high activity.

The first seven components were prepared from the naturally occurring peptide as was the sulfoxide form, designated with an "(O)."

Within the β-thymosin family, the actin-binding motif is known to be highly conserved. See, e.g., Huff et al., *Int. J. Biochem. Cell Biol.* 33:205-220 (2001). The majority of the heterogeneity of these molecules occurs at the carboxy terminus. Based on the conservation of the actin-binding sequence, and the fact that the other members of the β-thymosin family tested were active for endothelial cell migration and vessel sprouting, many similar variants and/or homologs of the sequences provided herein will be apparent to one of skill in the art for use in the disclosed methods. Moreover, because the in vitro activity for these and similar peptides against full-length thymosin $\beta_4$ peptide sequence (a gift of Dr. A. Goldstein, GWU, Washington D.C.). Primary antibody was detected using a Dako EnVision kit (DakoCytomation, Denmark) and counterstaining of sections was performed using hematoxylin.

Various modifications and variations of the described methods and compositions herein disclosed will be apparent to those skilled in the art without departing from the scope and spirit of the described principles. Although the invention has been described in connection with specific embodiments, it should be recognized that the illustrated embodiments are only particular examples of the disclosure and should not be taken as a limitation on the scope of the disclosure. Indeed, various modifications of the described modes for carrying out the invention which are obvious to those skilled in the relevant art and/or in molecular biology, dermatology, or related fields are intended to be within the scope of the present invention. Such a broad scope of the disclosure is in accord with the following claims. We therefore claim as our invention all that comes within the scope and spirit of these claims.

---

---

We claim:

1. A composition for promoting hair growth, wherein the composition comprises:
   (a) a polypeptide consisting of amino acids 1-26 of SEQ ID NO: 1;
   (b) a polypeptide consisting of amino acids 13-23 of SEQ ID NO: 1;
   (c) a polypeptide consisting of amino acids 7-43 of SEQ ID NO: 1;
   (d) a polypeptide consisting of amino acids 13-43 of SEQ ID NO: 1;
   (e) a polypeptide consisting of amino acids 10-28 of SEQ ID NO: 1;
   (e) a polypeptide consisting of amino acids 20-43 of SEQ ID NO: 1; or
   (f) a polypeptide consisting of amino acids 19-26 of SEQ ID NO: 1.

2. The composition of claim 1, further comprising a pharmaceutically suitable carrier.

3. The composition of claim 2, wherein the pharmaceutically suitable carrier is a topical pharmaceutical preparation.

4. The composition of claim 2, wherein the pharmaceutically suitable carrier comprises a hydrogel.

5. A method for enhancing hair growth in a subject in need thereof, comprising exposing a target area of skin of a subject to the composition of claim 1, wherein the target area is an area of alopecia-affected skin.

6. The method of claim 5, wherein the polypeptide is applied topically to an area of alopecia affected skin.

7. The method of claim 6, wherein the area of alopecia affected skin is a scalp of the subject.

8. The method of claim 5, wherein the subject is a human.

9. The method of claim 5, wherein the subject is a non-human animal.

* * * * *

UNITED STATES PATENT AND TRADEMARK OFFICE
CERTIFICATE OF CORRECTION

PATENT NO. : 7,563,766 B2  Page 1 of 1
APPLICATION NO. : 10/502115
DATED : July 21, 2009
INVENTOR(S) : Philp et al.

It is certified that error appears in the above-identified patent and that said Letters Patent is hereby corrected as shown below:

In the Specification:

Column 7, line 20, "MM-2" should read --MMP-2--

Column 7, line 32, "Gin Glu" should read --Gln Glu--

Column 7, line 33, "Gin Glu Lys Gin" should read --Gln Glu Lyn Gln--

Column 10, line 20, "His      Asn; Glu" should read --His     Asn; Gln--

Column 15, lines 13-14, "nu nu nude" should read --nu/nu nude--

Column 16, line 45, "atone" should read --alone--

Column 18, line 38, "nu nu female" should read --nu/nu female--

Column 18, line 38, "nu nu nude" should read --nu/nu nude--

Column 23, line 59, "2 hr" should read --2 hrs--

Column 25, line 11, "promotes" should read --promote--

Column 25, lines 15-16, "is contained" should read --contained--

Signed and Sealed this

Third Day of August, 2010

David J. Kappos
*Director of the United States Patent and Trademark Office*